United States Patent [19]

Kalindjian et al.

[11] Patent Number: 5,674,905
[45] Date of Patent: Oct. 7, 1997

[54] BICYCLOOCTANE AND BICYCLOHEPTANE DERIVATIVES

[75] Inventors: Sarkis Barret Kalindjian, Banstead; Caroline Minli Rachel Low, Croydon; Michael John Pether, Catford; Jonathan Michael Richard Davies, Beckenham; David John Dunstone, Plaistow; Iain Mair McDonald, Paddock Wood, all of United Kingdom

[73] Assignee: James Black Foundation Limited, London, United Kingdom

[21] Appl. No.: 351,320

[22] PCT Filed: Jun. 18, 1993

[86] PCT No.: PCT/GB93/01301

§ 371 Date: Dec. 19, 1994

§ 102(e) Date: Dec. 19, 1994

[87] PCT Pub. No.: WO94/00421

PCT Pub. Date: Jan. 6, 1994

[30] Foreign Application Priority Data

Jun. 19, 1992 [GB] United Kingdom ............... 9213094
Dec. 21, 1992 [GB] United Kingdom ............... 9226549

[51] Int. Cl.$^6$ ............... C07C 69/76; C07C 237/26; C07C 235/40
[52] U.S. Cl. ............... 514/616; 514/618; 514/620; 514/621; 514/381; 564/156; 564/162; 564/169; 564/165; 564/170; 564/172; 564/173; 548/253
[58] Field of Search ............... 564/156, 162, 564/165, 169, 170, 172, 173; 514/618, 620, 621, 616, 381; 548/253

[56] References Cited

U.S. PATENT DOCUMENTS 3,932,512  1/1976  Bharucha et al. ............... 260/570.9
5,141,937  8/1992  Siegel et al. ............... 514/237.5

FOREIGN PATENT DOCUMENTS 0 037 644  10/1981  European Pat. Off. .
0 308 839   3/1989  European Pat. Off. .
0 405 537   1/1991  European Pat. Off. .
0 455 195  11/1991  European Pat. Off. .

OTHER PUBLICATIONS

Kumar et al. "PMR Spectral Studies Of Diels–Alder Adducts: Anthracene–Crotonic Acid, Anthracene–Fumaric Acid & β–Naphthol–Fumaric Acid", *Indian J. Chem.*, vol. 23B:631–634, (1984).

Patent Abstract of Japan, vol. 014, No. 068, (C–686), Feb. 8, 1990, abstract of Kinoshita Seigo, "Production Of N–Substituted Norbornenedicarboximide Compound", Japanese 12 90 660, Nov. 22, 1989.

R. Bodmann et al., "Untersuchungen Zum Metabolismus Des Zentralen Analepticums Endomid Bei Der Ratte", *Pharmazie*, vol. 31:804–811, (1976).

Koch et al., "Thalidomid–Analoga", *Monatshefte fur chemie*, vol. 102:609–621, (1971).

Nagase, "Beitrage Zur Umlagerung Der Cyclischen Imidoester", *Umlagerung der Cyclischen Imidoester*, Bull. Chem. Soc. Jpn. vol. 37:1175–1180, (1964).

Waldmann, "Amino Acid Esters As Chiral Auziliaries in Lewis Acid Catalyzed Diels–Alder Reactions", *Liebigs Ann. Chem.*, pp. 671–680, (1990).

Waldmann, "(S)–Proline Benzyl Ester As Chiral Auxiliary In Lewis Acid Catalyzed Asymmetric Diels–Alder Reactions", *J. Org. Chem.*, vol. 53:6133–6136, (1988).

Koch et al. "Ueber Alkylierte Amide Bicyclischer Dicarbonsaeuren", *Monatshefte fur Chemie*, vol. 96:1928–1933, (1965).

Koch, "Ueber Alkylierte Amide Bicyclischer Dicarbonsaeuren", *J. Amer. Chem. Soc.*, vol. 94:406–409, (1963).

Brecknell et al., "Bicyclo[2.2.2]octane–2,5–carbolactone", *Australian Journal of Chemistry*, vol. 37, No. 11, pp. 232–2329, (1984).

Meek et al., "Some Diels–Alder Reactions Of Naphthacene", *J. Org. Chem.*, vol. 32:69–72, (1967).

Weisz et al., Org. Mass Spectrom., 24(1), 37–40. Jan. 1989.

Masuyama et al., Chem. Express, 3(2), 127–30. Mar. 1988.

Ito et al., J. Am. Chem. Soc., 104(26), 7609–22. Dec. 1982.

Plieninger et al., Chem. Ber., 109(6), 2121–25. Mar. 1976.

Takeda et al., Chem. Ber., 95, 2344–53. Dec. 1962.

*Primary Examiner*—Johann Richter
*Assistant Examiner*—Laura R. Cross
*Attorney, Agent, or Firm*—Foley & Lardner

[57] ABSTRACT

Compounds of formula (I), wherein A is selected from (a), (b), (c), (d), (e), (f) and B is selected from (g), (h), and (i), wherein W is a carbonyl, sulphonyl or sulphinyl group, and X is a carbonyl, sulphonyl or sulphinyl group or —C(O)—CH$_2$— (in which the carbonyl group is bonded to Y), provided that at least one of W and X contains carbonyl, Y is R$_9$—O— or R$_9$—N(R$_{10}$)—, Z is selected from (i), (ii), (iii), (iv) or Z is absent and W is H, with a number of provisions and phamaceutically acceptable salts thereof are ligands at CCK and/or gastrin receptors.

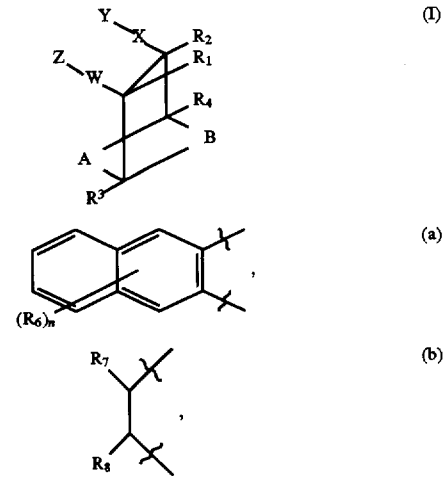

-continued $$\underset{R_8}{\overset{R}{>}}\!\!=\!\!< \quad \text{(c)}$$

$$\underset{H}{\overset{O}{\|}}\!\!-\!\!< \quad \text{(d)}$$

$$\underset{R_8}{\overset{R_7}{>}}\!\!< \quad \text{(e)}$$

$$\underset{R_8}{\overset{R_7}{>}}\!\!=\!\!< \quad \text{(f)}$$

$$>\!\!\underset{R_8}{\overset{R_7}{<}}\!\!< \quad \text{(g)}$$

$$>\!\!\underset{R_8}{\overset{R_7}{=}}\!\!< \quad \text{(h)}$$

-continued $$-\!\!\left\langle\!\!\bigcirc\!\!\right\rangle\!\!-(R_5)_m \quad \text{(i)}$$

$$-O-R_{11} \quad \text{(i)}$$

$$\underset{-N-H}{\overset{Q}{\|}} \quad \text{(ii)}$$

$$\underset{-N-(CH)_a-(CH_2)_b-\underset{R_{15}}{\overset{R_{14}}{\underset{|}{C}}}-Q'}{\overset{Q}{\underset{|}{\|}}}\quad \text{(iii)}$$
$$\phantom{-N-(CH)_a-(CH_2)_b-C}\underset{T}{\overset{|}{G}}$$

$$\underset{-N}{\overset{R_{17}}{\underset{|}{N}}}\!\!-\!\!\underset{R_{19}}{\overset{R_{18}}{\underset{|}{C}}}\!\!-\!\!\underset{}{\overset{O}{\underset{\|}{C}}}\!\!-\!\!N\!\!-\!\!R_{12}\!\!-\!\!COOR_{11} \quad \text{(iv)}$$

7 Claims, No Drawings

BICYCLOOCTANE AND BICYCLOHEPTANE DERIVATIVES

This is a 371 of PCT/GB93/0101 filed Jun. 18, 1993. This invention relates to bicyclooctane and bicycloheptane derivatives, and more particularly to bicyclooctane and bicycloheptane derivatives which bind to cholecystokinin (CCK) and/or gastrin receptors. The invention also relates to methods for preparing such bicyclooctane and bicycloheptane derivatives and to compounds which are useful as intermediates in such methods.

Gastrin and the CCK's are structurally-related neuropeptides which exist in gastrointestinal tissue and in the CNS (see Mutt V., *Gastrointestinal Hormones*, Glass G. B. J., ed., Raven Press, N.Y., p 169 and Nisson G., ibid, p. 127).

Gastrin is one of the three primary stimulants of gastric acid secretion. Several forms of gastrin are found including 34-, 17-, and 14-amino acid species with the minimum active fragment being the C-terminal tetrapeptide (TrpMetAspPhe—NH$_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-NH2) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to cholecystokinin and/or gastrin receptors are important because of their potential pharmaceutical use as antagonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lowered gastrin activity is desirable. The hormone has also been shown to have a trophic action on cells in the stomach and so an antagonist may be expected to be useful in the treatment of cancers, particularly in the stomach.

Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for cholecystokinin receptors in the brain (so-called CCK$_B$receptors) have been claimed to possess anxiolytic activity.

According to the present invention, medicaments for counteracting an effect of cholecystokinin or gastrin in a patient are prepared using a compound of the formula

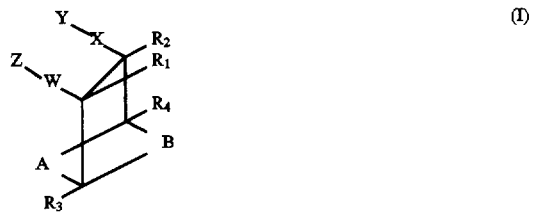

wherein A is selected from

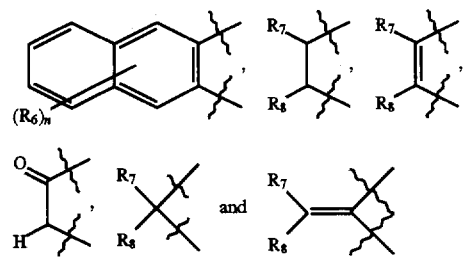

and B is selected from

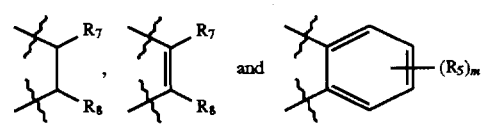

(provided that A is not

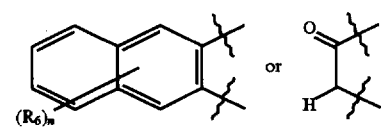

when B is

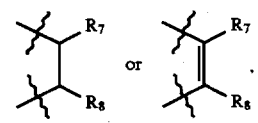

, and A is not

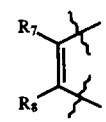

when B is

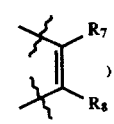

)

wherein

W is a carbonyl, sulphonyl or sulphinyl group, and X is a carbonyl, sulphonyl or sulphinyl group or —C(O)—

$CH_2$— (in which the carbonyl group is bonded to Y), provided that at least one of W and X contains carbonyl Y is $R_9$—O— or $R_9$—$N(R_{10})$— (wherein $R_9$ is H or $C_1$ to $C_{15}$ hydrocarbyl, up to two carbon atoms of the hydrocarbyl moiety optionally being replaced by a nitrogen, oxygen or sulphur atom provided that Y does not contain a —O—O— group, and $R_{10}$ is H, $C_1$ to $C_3$ alkyl, carboxymethyl or esterified carboxymethyl), Z is selected from i) —O—$R_{11}$ wherein $R_{11}$ is H, $C_1$ to $C_5$ alkyl, phenyl, substituted phenyl, benzyl or substituted benzyl;

ii)

wherein Q is H, $C_1$ to $C_5$ hydrocarbyl, or -$R_{12}$-U, wherein $R_{12}$ is a bond or $C_1$ to $C_3$ alkylene and U is aryl, substituted aryl, heterocyclic, or substituted heterocyclic, iii)

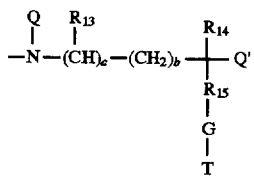

wherein a is 0 or 1 and b is from 0 to 3, $R_{13}$ is H or methyl, $R_{14}$ is H or methyl; or $R_{14}$ is $CH_2$= and Q' is absent; or $R_{13}$ and $R_{14}$ are linked to form a 3- to 7-membered ring, $R_{15}$ is a bond or $C_1$ to $C_5$ hydrocarbylene, G is a bond, —CHOH— or —C(O)—

Q' is as recited above for Q or —$R_2$—$(C(O))_d$—L—$(C(O))_e$—$R_{11}$ (wherein $R_{11}$ and $R_{12}$ are as defined above, L is O, S or —$N(R_{16})$—, in which $R_{16}$ is as defined above for $R_{10}$, and d and e are 0 or 1, provided that d+e<2); or Q' and $R_{14}$, together with the carbon atom to which they are attached, form a 3- to 7-membered ring, Q is as defined above; or Q and $R_4$ together form a group of the formula —$(CH_2)_f$—V—$(CH_2)_g$— wherein V is —S—, —S(O)—, —$S(O)_2$—, —$CH_2$—, —CHOH— or —C(O)—, f is from 0 to 2 and g is from 0 to 3; or, when Q' is —$R_{12}$—U and U is an aromatic group, Q may additionally represent a methylene link to U, which link is ortho to the $R_{12}$ link to U, T is H, cyano, $C_1$ to $C_4$ alkyl, —$CH_2OH$, carboxy, esterified carboxy, amidated carboxy or tetrazolyl; or iv)

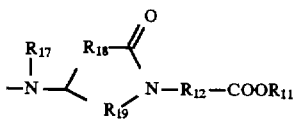

wherein $R_{11}$ and $R_{12}$ are as defined above, $R_{17}$ is as defined above for $R_{10}$, and $R_{18}$ and $R_{19}$ are independently a bond or $C_1$ to $C_3$ alkylene, provided that $R_{18}$ and $R_{19}$ together provide from 2 to 4 carbon atoms in the ring, or Z is absent and W is H, $R_1$ is H, methyl, halo, carboxy, esterified carboxy, amidated carboxy, tetrazolyl, carboxymethyl, esterified carboxymethyl, amidated carboxymethyl or tetrazolylmethyl, $R_2$ is selected from the groups recited above for $R_1$; or, when Z is absent and W is H, $R_2$ may additionally represent —C(O)—Z' wherein Z' is selected from the groups recited above for Z; or $R_1$ and $R_2$ together form a second bond between the carbon atoms to which they are attached, $R_3$ and $R_4$ are independently selected from hydrogen, halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_5$ and $R_4$ (or each $R_5$ and $R_6$ group, when m or n is 2 or more) are independently selected from halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_5$ and $R_6$ are independently selected from hydrogen, $C_1$ to $C_5$ alkyl, phenyl, benzyl, substituted phenyl and substituted benzyl, m is from 0 to 4, provided that m is not more than 2 unless $R_5$ is exclusively halo, n is from 0 to 4, provided that n is not more than 2 unless $R_5$ is exclusively halo, or a pharmaceutically acceptable salt thereof.

Compounds according to formula (I) above are believed to be novel per se, provided that -Z is not absent, -W-Z is not equal to -X-Y, and A or B contains at least one aromatic ring, and further provided that the compound is not 7-(methylaminocarbonyl)-2-diphenylmethylene bicyclo[2.2.1] hept-4-ene-6-carboxylic acid or endo 7-(phenethylaminocarbonyl)-2-diphenylmethylene bicyclo [2.2.1] hept-4-ene-6-carboxylic acid.

The compounds of the invention exist in various enantiomeric and diastereomeric forms as a result of the asymmetric carbon atoms to which W and X are attached. It will be understood that the invention comprehends the different enantiomers and diastereomers in isolation from each other, as well as mixtures of enantiomers. Also, the structural formulae herein show the groups W and X arranged cis to each other, but it will be appreciated that the invention includes the corresponding trans isomers. Similarly, the invention includes the different regioisomers which result from W and X being arranged in different configurations relative to A. That is to say, the invention comprehends both the exo and the endo isomers of the compounds represented by the above formula. In this specification, the designation exo and endo is determined by the convention described in "Vocabulary of Organic Chemistry", Orchin et al (eds.), Wiley, New York (1980) p141. For example, in the benzo-fused compounds of the invention, the exo isomer has the 7 and 8 substituents on the opposite side of the molecule to this aromatic ring.

The term "hydrocarbyl", as used herein, refers to monovalent groups consisting of carbon and hydrogen. Hydrocarbyl groups thus include alkyl, alkenyl, and alkynyl groups (in both straight and branched chain forms), cycloalkyl (including polycycloalkyl), cycloalkenyl, and aryl groups, and combinations of the foregoing, such as alkylaryl, alkenylaryl, alkynylaryl, cycloalkylaryl, and cycloalkenylaryl groups.

A "carbocyclic" group, as the term is used herein, comprises one or more closed chains or rings, which consist entirely of carbon atoms. Included in such groups are alicyclic groups (such as cyclopropyl, cyclobutyl, cyclopentyl, cyclohexyl and adamantyl), groups containing both alkyl and cycloalkyl moieties (such as methyl adamantyl), and aromatic groups (such as phenyl, naphthyl, indanyl, fluorenyl, (1,2,3,4)-tetrahydronaphthyl, indenyl and isoindenyl).

The term "aryl" is used herein to refer to aromatic carbocyclic groups, including those mentioned above.

A "heterocyclic" group comprises one or more closed chains or rings which have at least one atom other than carbon in the closed chain or ring. Examples include thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

The term "halogen", as used herein, refers to any of fluorine, chlorine, bromine and iodine. Most usually, however, halogen substituents in the compounds of the invention are chlorine or fluorine substituents.

When reference is made herein to a "substituted" aromatic group, the substituents will generally be from 1 to 3 in number (and more usually 1 or 2 in number), and selected from the groups recited above for $R_5$.

Preferably, m and n are both 0. However, when m and n are not both 0, $R_5$ and $R_6$ are preferably selected from halo, amino, nitro, cyano, sulphamoyl, $C_1$ to $C_3$ alkyl and $C_1$ to $C_3$ alkoxy. As mentioned above, when m or n is 2 or more, each $R_5$ and $R_6$ group is independent of the others. For example, the compounds of the invention may include two different $R_5$ groups.

Particularly preferred groups for $R_3$ and $R_4$ are hydrogen and the groups just recited for $R_5$, and especially hydrogen, methyl and fluoro.

An "esterified" carboxy group, as the term is used herein, is preferably of the form —$COOR_{20}$, wherein $R_{20}$ is $C_1$ to $C_5$ alkyl, phenyl, substituted phenyl, benzyl, substituted benzyl, or one of the following:

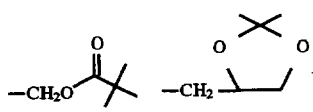

Most commonly, $R_{20}$ is $C_1$ to $C_5$ alkyl, benzyl or substituted benzyl, and particularly $C_1$ to $C_5$ alkyl. Similarly, an "amidated" carboxy group is preferably of the form —$CONR_{21}R_{22}$ wherein $R_{21}$ and $R_{22}$ are independently H, $C_1$ to $C_5$ alkyl, phenyl, substituted phenyl, benzyl or substituted benzyl.

In the case of the group T, preferred amidated carboxy groups take the form —$CONR_{21}R_{22}$ (wherein $R_{21}$ and $R_{22}$ are as defined above) or

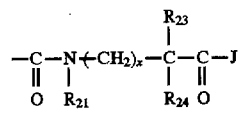

wherein $R_{21}$ is as defined above, $R_{23}$ and $R_{24}$ are independently H or methyl, or $R_{23}$ and $R_{24}$ (together with the carbon atom to which they are attached) form a 3- to 7-membered carbocyclic group, J is —OH, —O—$R_{20}$ or —$NHR_{22}$, wherein $R_{20}$ and $R_{24}$ are as defined above, and x is 0 to 3.

When $R_{13}$ and $R_{14}$ are linked to form a ring, such ring will generally be saturated, and usually also carbocyclic. Similarly, when Q' and $R_{14}$ are linked to form a ring, this will also usually be saturated and carbocyclic.

Exemplary carbocyclic and heterocyclic groups which may form the group U include:

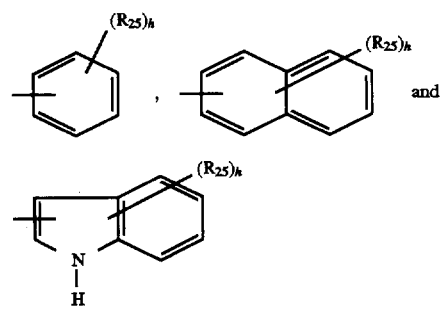

wherein $R_{25}$ is as defined above for $R_5$, and h is from 0 to 3, and

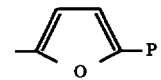

wherein P is H or —$COOR_{26}$, in which $R_{26}$ is as defined above for $R_{21}$.

Z is preferably —$NH_2$, —O—$R_{11}$ or

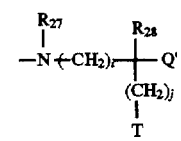

wherein i is from 0 to 4, j is from 0 to 3, $R_{27}$ and $R_{28}$ are independently H or methyl, or $R_{27}$ and $R_{28}$ together form a group of the formula —$(CH_2)_k$—V'—$CH_2$— (wherein V' is —$CH_2$—, —CHOH— or —C(O)—, and k is 0 to 2). Most commonly, i is 0 or 1 and j is 0 to 2.

When W is sulphinyl, Y is preferably $R_9$—NH—.

Preferably, $R_9$ is $C_6$ to $C_8$ straight or branched chain alkyl, or $R_{29}$—$(CH_2)_p$—, wherein $R_{29}$ is selected from phenyl, 1-naphthyl, 2-naphthyl, indolyl, norbornyl, adamantyl or cyclohexyl, and p is from 0 to 3.

Compounds according to the present invention in which W is a carbonyl group, X is carbonyl or sulphonyl, and Z is OH may conveniently be made by the process depicted in Reaction Scheme A.

Reaction Scheme A

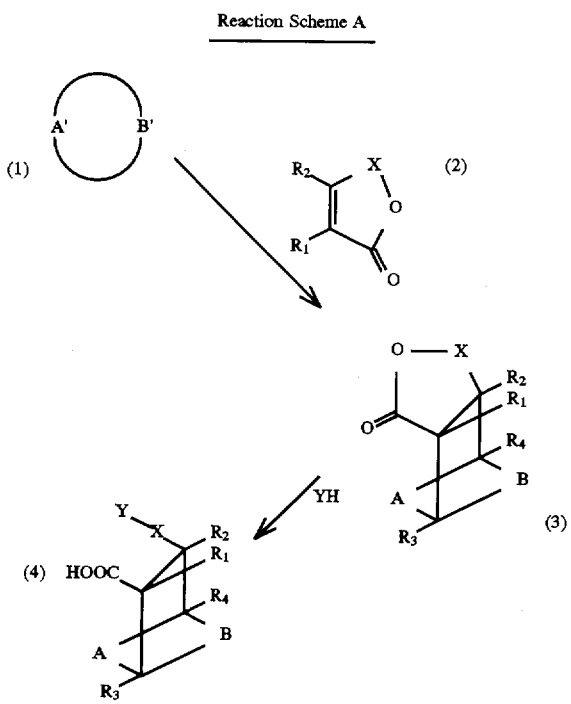

In this scheme, and in Reaction Schemes B, C and D below, A' is selected from

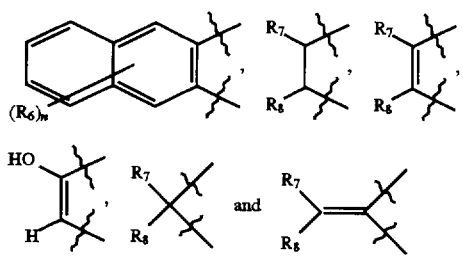

and B' is selected from

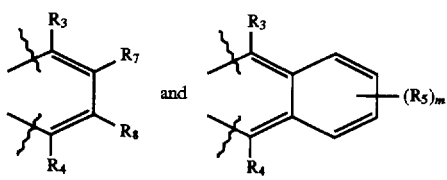

(provided that A' is not

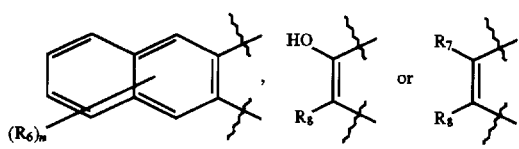

when B' is

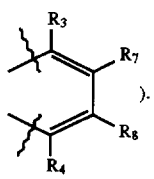

).

In Reaction Scheme A, compound (1)(e.g. naphthalene or 2,3-dimethylnaphthalene) is reacted with the acid anhydride (2) in a Diels-Alder reaction. The reactants are conveniently refluxed together in a suitable solvent such as toluene to form the adduct (3). In some cases, it may be appropriate to conduct the reaction at elevated pressure and/or in the presence of a Lewis acid catalyst. The adduct (3) is then reacted with a compound of the formula YH (ie. either an alcohol or an amine) to form the acid compound (4). If YH is an amine, the reaction is suitably carried out in a solvent such as THF in the presence of a catalytic amount of DMAP. If YH is an alcohol, the reaction may be conducted in pyridine at elevated temperature.

The invention therefore also provides a method of making compounds wherein W is carbonyl and X is carbonyl or sulphonyl, said method including the step of reacting a compound of the formula

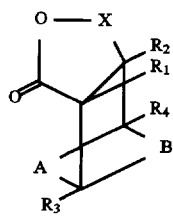

with a compound of formula YH.

The equivalent trans adducts can be prepared using a suitably differentiated fumaric acid (eg. the mono methyl mono benzyl diester), which, after addition to compound (1), allows independent elaboration of the two side chains.

In those cases in which the Diels Alder reaction leads to a bicyclooctene or a bicycloheptene, the corresponding bicyclooctane or bicycloheptane can be obtained, if desired, by catalytic hydrogenation under appropriate conditions (preferably using a platinum catalyst), usually as the final step in the procedure.

Compounds in which Z is other than OH may of course be made from the acid compound (4) by conventional esterification or amidation reactions. Suitable amidation methods are described in detail in "The Peptides, Vol. 1", Gross and Meinenhofer, Eds., Academic Press, N.Y., 1979. These include the carbodiimide method (using, for example, 1,3-dicyclohexylcarbodiimide [DCC] or 1-(3-dimethylaminopropyl)-3-ethylcarbodiimide hydrochloride [EDCI], and optionally an additive such as 1-hydroxybenzotriazole [HOBT] to prevent racemization), the azide method, the mixed anhydride method, the symmetrical anhydride method, the acid chloride method, the acid bromide method, the use of bis (2-oxo-3-oxazolidinyl) phosphinic chloride [BOP-Cl], the use of PyBOP, the use of the isopropenylsuccinimido carbonate method and the active ester method (using, for example, N-hydroxysuccinimide esters, 4-nitrophenyl esters or 2,4,5-trichlorophenol esters).

The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

A procedure analogous to that shown in reaction scheme A may also be used as the basis for preparing the compounds of the invention in which W is sulphonyl and Y is $R_9$—O—, as depicted in reaction scheme B below:

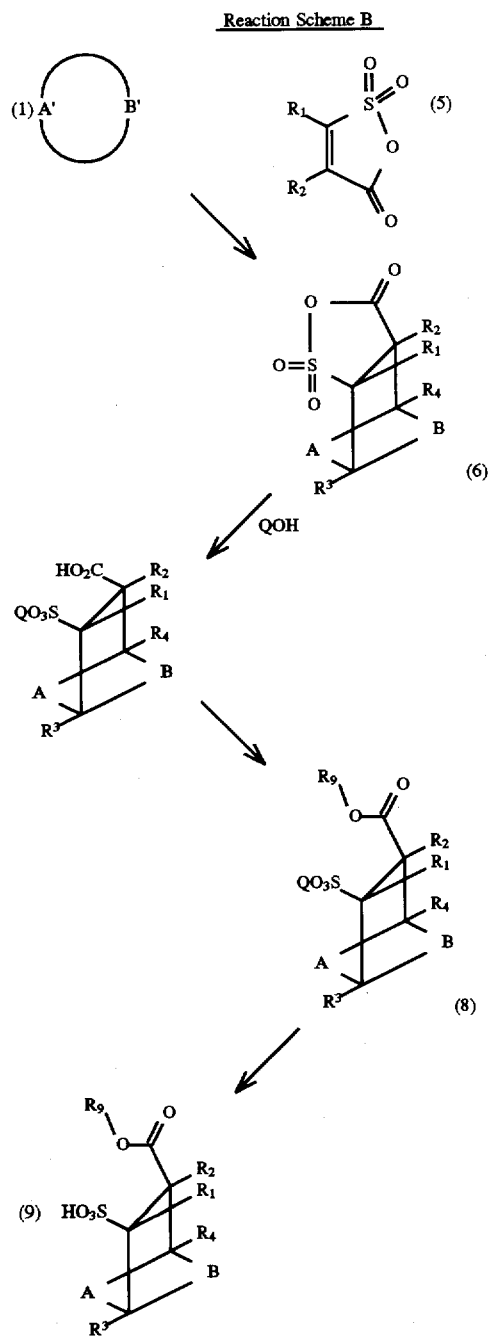

In this case, the Diels-Alder adduct (6) is opened with an alcohol such as benzyl alcohol (represented as QOH), so that product (7) is the corresponding sulphonyl ester. The free carboxylic acid group of this sulphonyl ester may then be esterified by conventional methods, followed by hydrogenolysis of the product (8) to yield the desired sulphonic acid carboxylic ester (9);

The compounds of the invention in which W is sulphonyl and Y is $R_9$—NH— may be prepared by analogous means, in which compound (7) is amidated (rather than esterified) prior to hydrogenolysis. Alternatively, a process such as is depicted in reaction scheme C may be employed:

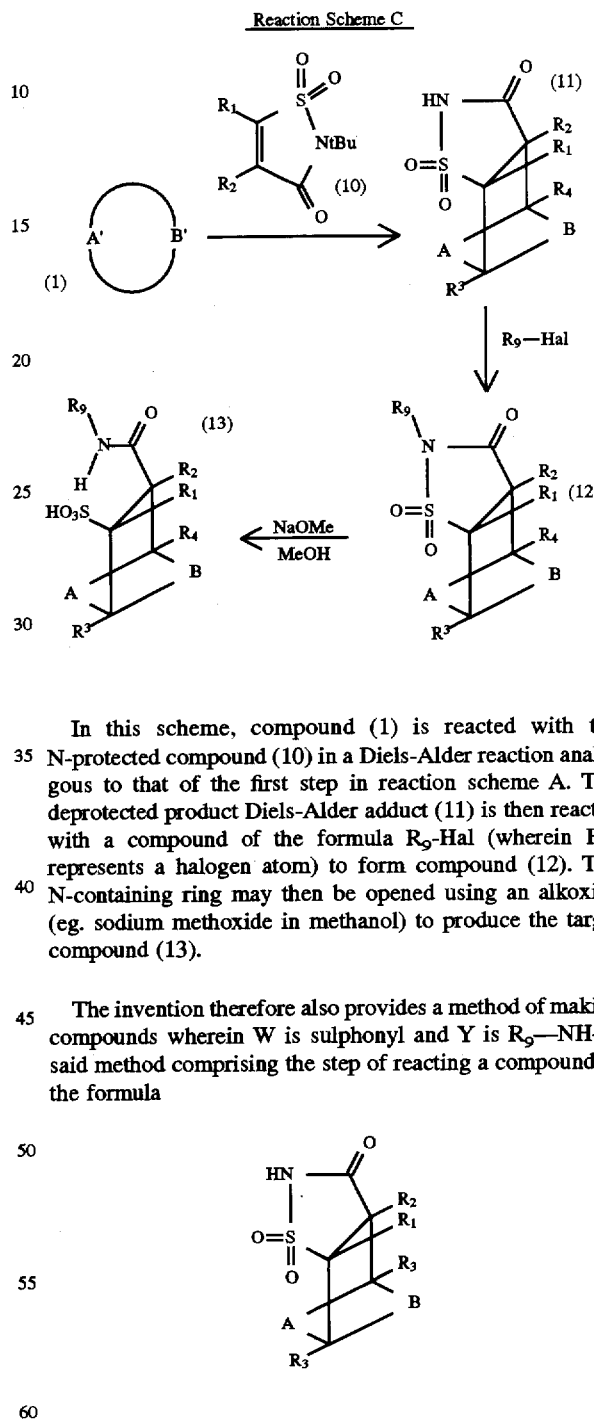

In this scheme, compound (1) is reacted with the N-protected compound (10) in a Diels-Alder reaction analogous to that of the first step in reaction scheme A. The deprotected product Diels-Alder adduct (11) is then reacted with a compound of the formula $R_9$-Hal (wherein Hal represents a halogen atom) to form compound (12). The N-containing ring may then be opened using an alkoxide (eg. sodium methoxide in methanol) to produce the target compound (13).

The invention therefore also provides a method of making compounds wherein W is sulphonyl and Y is $R_9$—NH—, said method comprising the step of reacting a compound of the formula

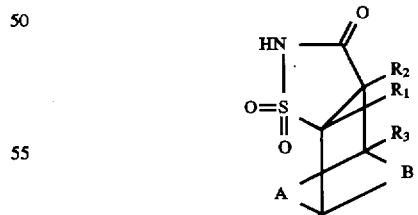

with a compound of the formula $R_9$-Hal, and then reacting the product with an alkoxide.

Compounds of the invention wherein W or X is a sulphoxide group may conveniently be prepared by the route shown in reaction scheme D:

Reaction Scheme D

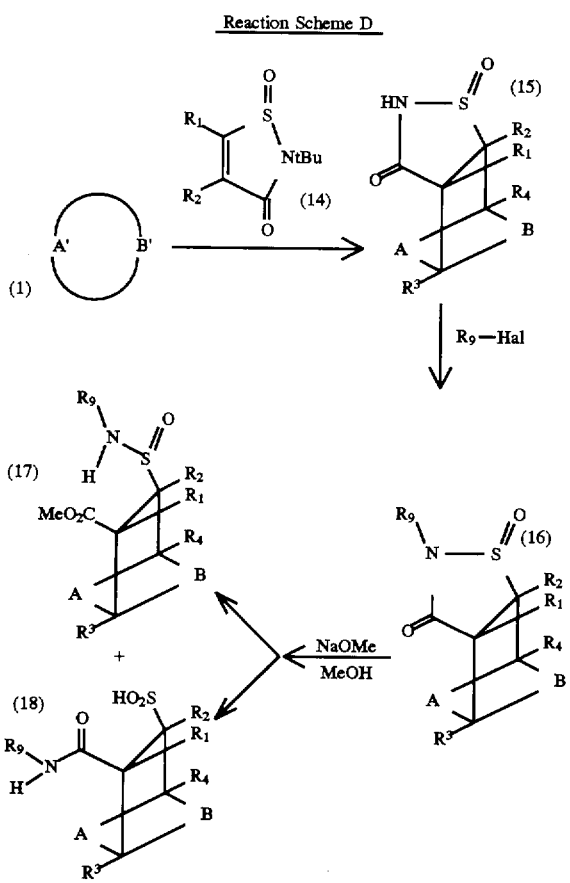

Reaction scheme D is analogous to reaction scheme C, except that the sulphoxide analogue of compound (10) is used in the Diels-Alder reaction, to yield the sulphoxide analogue of adduct (12). This can then be opened both ways to give on the one hand the sulphinamide acid alkyl ester (17), and on the other the sulphinic acid amide (18). The free sulphinamide acid can of course be obtained from the alkyl ester (12) by conventional methods.

Accordingly, the invention also provides a method of making compounds wherein W or X is sulphoxide, said method comprising the step of reacting a compound of the formula:

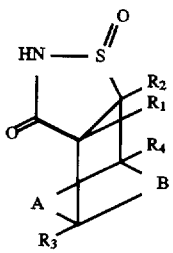

with a compound of the formula $R_9$-Hal, and then reacting the product with an alkoxide.

While reaction schemes C and D above lead to the free sulphonic or sulphinic acid compounds, it will be appreciated that the corresponding ester or amide derivatives can be prepared from the free acid compounds by conventional methods. Most usually, coupling of the sulphonic or sulphinic acid compounds will be via the corresponding sulphonic or sulphinic acid chlorides.

Pharmaceutically acceptable salts of the acidic or basic compounds of the invention can of course be made by conventional procedures, such as by reacting the free base or acid with at least a stoichiometric amount of the desired salt-forming acid or base.

The compounds of the invention can be administered by oral or parenteral routes, including intravenous, intramuscular, intraperitoneal, subcutaneous, rectal and topical administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated With a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinylpyrrolidone and gum tragacanth, and a wetting agent such as lecithin. Suitable preservatives for aqueous suspensions include ethyl and n-propyl p-hydroxybenzoate.

The invention is now further illustrated by means of the following examples.

EXAMPLE 1

Preparation of exo-(±)-cis-8-(1-adamantylmethylaminocarbonyl)-5,6-benzobicyclo[2.2.2]oct-2-ene-7-carboxylic acid a. exo and endo 5,6-benzobicyclo[2.2.2]oct-2-ene-7,8-dicarboxylic anhydride Naphthalene (306.5 g, 2.39 mol) and maleic anhydride (469 g, 4.78 mol) were heated at 120° for 24 h in a Parr bomb. After reaction the mixture was poured into water and the insoluble material filtered and dried. The dry solid was dissolved in hexane and the insoluble material filtered, washed with hexane and dried in vacuo. The overall yield at this stage was 17.13 g (3.2%). The exo and endo regioisomers were separated by column chromatography (silica 30% ethyl acetate and 70% hexane) to give exo isomer (high $R_f$) 6.05 g, and endo isomer (lower $R_f$) 6.15 g.

b. exo-(±)-cis-8-(1-adamantylmethylaminocarbonyl)-5,6-benzobicyclo[2.2.2]oct-2-ene-7-carboxylic acid The exo isomer prepared in step a. (150 mg, 0.66 mmol) was dissolved in THF (10 ml) and 1-adamantylmethylamine (110 mg, 0.66 mmol) was added. The mixture was stirred at room temperature for 2 h and the precipitate was filtered and washed with THF (10 ml) and hexane (20 ml) and dried to leave the title compound (0.253 g, 97%). The compound was characterised and tested as the N-methyl-D-glucamine salt.

Found: C, 63.59; H, 8.12; N, 4.73. $C_{32}H_{46}N_2O_8 \cdot 1.26H_2O$ requires C, 63.28; H, 7.72; N, 4.61%.

EXAMPLE 2

Preparation of endo-(±)-cis-8-(1-adamantylmethylaminocarbonyl)-5,6-benzobicyclo[2.2.2]oct-2-ene-7-carboxylic acid The compound was prepared essentially as in example 1 using the endo isomer (isolated in step a.) instead of the exo isomer as the substrate in step b. for reaction with 1-adamantylmethylamine. Yield step b. 95%. The compound was characterised and tested as the N-methyl-D-glucamine salt. Found: C, 63.04; H, 7.97; N, 4.50. $C_{32}H_{46}N_2O_8 \cdot 1.32H_2O$ requires C, 62.95; H, 8.03; N, 4.59%.

EXAMPLE 3

Preparation of exo-(±)-cis8-(1-cyclohexylmethylaminocarbonyl)-5,6-benzobicyclo[2.2.2]oct-2-ene-7-carboxylic acid This was prepared essentially as in example 1 but using cyclohexylmethylamine instead of 1-adamantylmethylamine in step b. Yield step b. 96%. The compound was characterised and tested as the N-methyl-D-glucamine salt. Found: C, 61.88; H, 8.24; N, 5.01. $C_{28}H_{42}N_2O_8 \cdot 0.57H_2O$ requires C, 61.72; H, 7.98; N, 5.14%.

EXAMPLE 4

Preparation of endo-(±)-cis-8-(1-cyclohexylmethylaminocarbonyl)-5,6-benzobicyclo[2.2.2]oct-2-ene-7-carboxylic acid This was prepared essentially as in example 2 but using cyclohexylmethylamine instead of 1-adamantylmethylamine in step b. Yield step b. 72%. The compound was characterised and tested as the N-methyl-D-glucamine salt. Found: C, 62.82; H, 8.01; N, 5.07. $C_{28}H_{42}N_2O_8$ requires C, 62.90; H, 7.92; N, 5.24%.

EXAMPLE 5

Preparation of exo-(±)-cis-8-(octylaminocarbonyl)-5,6-benzobicyclo[2.2.2]oct-2-ene-7-carboxylic acid This was prepared essentially as in example 1 but using octylamine instead of 1-adamantylmethylamine in step b. Yield step b. 51%. The compound was characterised and tested as the N-methyl-D-glucamine salt. Found: C, 63.19; H, 8.61; N, 5.15. $C_{29}H_{46}N_2O_8$ requires C, 63.25; H, 8.42; N, 5.09%.

EXAMPLE 6

Preparation of endo-(±)-cis-8-(octylamino-carbonyl)-5,6-benzobicyclo[2.2.2]oct-2-ene-7-carboxylic acid This was prepared essentially as in example 2 but using octylamine instead of 1-adamantylmethylamine in step b. Yield step b. 58%. The compound was characterised and tested as the N-methyl-D-glucamine salt. Found: C, 63.18; H, 8.59; N, 5.08. $C_{29}H_{46}N_2O_8$ requires C, 63.25; H, 8.42; N, 5.09%.

EXAMPLE 7

Preparation of exo-cis-7-(1-S-methoxycarbonylethylaminocarbonyl)-8-(1-adamantylmethylaminocarbonyl)-5,6-benzobicyclo[2.2.2]oct-2-ene (mixture of diastereomers)

The product of example 1 (200 mg, 0.51 mmol), PyBOP (266 mg) and diisopropylethylamine (0.267 ml, 1.53 mmol) were dissolved in dry dichloromethane and stirred at room temperature for 1 h. L-alanine methyl ester hydrochloride (71 mg, 0.51 mmol) was added and the reaction mixture stirred at room temperature overnight. The reaction mixture was washed with 2M hydrochloric acid and filtered through a silica pad eluted with 20% ethyl acetate and dichloromethane (50 ml). The organic layer was evaporated in vacuo to yield the title compound as a colourless solid (109 mg, 45%). Found: C, 72.79; H, 7.63; N, 5.62. $C_{29}H_{36}N_2O_4$ requires C, 73.08; H, 7.61; N, 5.88%.

EXAMPLE 8

Preparation of endo-cis-7-(1—S—methoxycarbonylethylaminocarbonyl)-8-(1-adamantylmethylaminocarbonyl)-5,6-benzobicyclo[2.2.2]oct-2-ene (mixture of diastereomers)

The compound was prepared essentially as in example 7 but using the product of example 2 as substrate instead of the product of example 1. Yield 43% Found: C, 71.10; H, 7.75; N, 5.49. $C_{29}H_{36}N_2O_4 \cdot 0.78 H_2O$ requires C, 70.99; H, 7.72; N, 5.71%.

EXAMPLE 9

Preparation of exo-cis-7-(2-R-carboxyl-pyrrolidinocarbonyl)-8-(1-adamantylmethylaminocarbonyl)-5,6-benzobicyclo[2.2.2]oct-2-ene (mixture of diastereomers)

a. exo-cis-7-(2-R-benzyloxycarbonyl-pyrrolidinocarbonyl)-8-(1-adamantylmethylaminocarbonyl)-5,6-benzobicyclo[2.2.2]oct-2-ene (mixture of diastereomers)

The reaction was performed essentially as in example 7 but using D-proline benzyl ester hydrochloride instead of L-alanine methyl ester hydrochloride. Yield 65% b. exo-cis-7-(2-R-carboxy-pyrrolidinocarbonyl)-8-(1-adamantylmethylaminocarbonyl)-5,6-benzobicyclo-[2.2.2]oct-2-ene (mixture of diastereomers)

The product of step a. (150 mg, 0.26 mmol) was dissolved in ethanol and 10% palladium on charcoal (15 mg) was added. The reaction mixture was stirred under an atmosphere of hydrogen gas at room temperature overnight. The reaction mixture was filtered through a pad of celite and evaporated to give a gum. This material was redissolved in dichloromethane and on evaporation gave the title compound as a white solid. Yield 75% Found: C, 70.36; H, 7.83; N, 5.44. $C_{30}H_{36}N_2O_4 \cdot 1.39 H_2O$ requires C, 70.15; H, 7.61; N, 5.45%.

EXAMPLE 10

Preparation of endo-cis-7-(2-R-carboxy-pyrrolidinocarbonyl)-8-(1-adamantylmethylaminocarbonyl)-5,6-benzobicyclo[2.2.2]oct-2-ene (mixture of diastereomers)

The compound was prepared essentially as in example 9 but using the product of example 2 instead of the product of example 1 in step a. Yield overall for steps a and b 60%. Found: C, 68.97; H, 7.55; N, 5.33. $C_{30}H_{36}N_2O_4$ requires C, 69.08; H, 7.66; N, 5.37%.

EXAMPLE 11

Preparation of exo-(±)-cis-8-(1-adamantylmethylaminocarbonyl)-2,3-dimethyl-5,6-benzobicyclo[2.2.2]oct-2-ene-7-carboxylic acid a. exo and endo 2,3-dimethyl-5,6-benzobicyclo[2.2.2]oct-2-ene-7,8-dicarboxylic anhydride 2,3-dimethylnaphthalene (5.42 g, 35 mmol) and maleic anhydride (3.40 g, 35 mmol) were dissolved in dichloromethane (250 ml) and aluminium chloride (4.62 g, 35 mmol) was added. The reaction mixture was stirred at room temperature for 4 h and then was poured onto ice. The two layers were separated and the dichloromethane layer was washed with saturated brine (3×100 ml) and then dried. This layer was evaporated to leave a yellow solid which was recrystallised from ether to give a 1:1 mixture of the endo and exo regioisomers. Column chromatography (silica 30% ethyl acetate and hexane) gave pure exo isomer (high $R_f$)(0.15 g) but no significant amounts of endo isomer could be isolated pure.

b. exo-(±)-cis-8-(1-adamantylmethylaminocarbonyl)-2,3-dimethyl-5,6-benzobicyclo[2.2.2]oct-2-ene-7-carboxylic acid This was carried out essentially as described in example 1 step b. but using the exo anhydride isolated in step a. above. Yield step b. 91%. The compound was characterised and tested as the N-methyl-D-glucamine salt. Found: C, 64.38; H, 8.29; N, 4.31. $C_{34}H_{50}N_2O_8$. $1.06H_2O$ requires C, 64.42; H, 8.29; N, 4.42%.

EXAMPLE 12

Preparation of endo-(±)-cis-8-(1-adamantylmethylaminocarbonyl)-2,3-dimethyl -5,6-benzobicyclo[2.2.2]oct-2-ene-7-carboxylic acid This was prepared essentially as in example 11 using the 1:1 exo:endo mixture prepared in step a. of example 11 rather than the pure exo regioisomer in step b. The desired endo isomer, the title compound, precipitated out of solution and was isolated by filtration and recrystallisation. Yield step b. 48%. The compound was characterised and tested as the N-methyl-D-glucamine salt. Found: C, 64.54; H, 8.24; N, 4.39. $C_{34}H_{50}N_2O_8$. $0.98H_2O$ requires C, 64.57; H, 8.28; N, 4.43%.

EXAMPLE 13

Preparation of endo-(±)-cis-8-(1-adamantylmethylaminocarbonyl)-2-oxo-5,6-benzobicyclo[2.2.2]octane-7-carboxylic acid a. endo (±)-2-oxo-5,6-benzobicyclo[2.2.2]oct-2-ene-7,8-dicarboxylic anhydride 2-Naphthol (20 g, 0.14 mol) and maleic anhydride (18.0 g, 1.8 mol) were heated at 220° in a Parr apparatus for 30 min. On cooling ethyl acetate (60 ml) was added and the red gum formed during heating gradually dissolved and a colourless solid began to precipitate. This was filtered and washed with ethyl acetate (30 ml) and hexane (100 ml) and dried in vacuo to yield the title compound as the endo isomer (4.33 g, 13%), m.p. 194°–5°.

b. endo-(±)-cis-8-(1-adamantylmethylaminocarbonyl)-2-oxo-5,6-benzobicyclo[2.2.2]octane-7-carboxylic acid This was prepared essentially as described in example 1 step b. but using the oxo anhydride prepared in step a. above instead of the exo anhydride described in example 1 step a. Yield step b. 75%). The compound was characterised and tested as the N-methyl-D-glucamine salt. Found: C, 61.86; H, 7.74; N, 4.53. $C_{32}H_{46}N_2O_9$. $1.00H_2O$ requires C, 61.92; H, 7.79; N, 4.51%.

EXAMPLE 14

Preparation of endo and exo cis-(±)-8-(1-adamantylmethylaminocarbonyl)-2,3-benzo-5,6-(2,3-naphtho)bicyclo[2.2.2]octane-7-carboxylic acid a. endo and exo 2,3-benzo-5,6-(2,3-naphtho)-bicyclo[2.2.2] octane-7,8-dicarboxylic anhydride 2,3-benzanthracene (1.0 g, 4.4 mmol) and maleic anhydride (0.43 g, 4.4 mmol) were dissolved in toluene (20 ml) and heated at reflux for 2.5 h under an atmosphere of argon. The reaction was cooled to room temperature and crystals precipitated which were filtered and washed with toluene and hexane before being dried in vacuo. The anhydride was isolated as an inseparable mixture of endo and exo isomers (1.13 g, 79%).

b. endo and exo cis-(±)-8-(1-adamantylmethylaminocarbonyl)-2,3-benzo-5,6-(2,3-naphtho)bicyclo[2.2.2]octane-7-carboxylic acid The reaction was performed essentially as in Example 1 using the anhyride produced in step a. above as substrate instead of the exo isomer produced in Example 1 step a. The compound was characterised and tested as the N-methyl glucamine salt. Found: C, 66.28; H, 7.39; N, 3.92. $C_{40}H_{50}N_2O_8$. $2H_2O$ requires C, 66.43; H, 7.53; N, 3.87%.

EXAMPLE 15

Preparation of endo-cis-7-(2-R-(3-indolyl)-1-carboxy-ethylaminocarbonyl)-8-(1-adamantylmethylaminocarbonyl)-5,6-benzobicyclo[2.2.2]oct-2-ene (Diastereomer 1)

a. endo-cis-7-(2-R-(3-indolyl)-1-benzyloxycarbonyl-ethylaminocarbonyl)-8-(1-adamantylmethylaminocarbonyl)-5,6-benzobicyclo[2.2.2]oct-2-ene and separation of diastereomers The mixture of diastereomers was prepared essentially as in example 8 but using the trifluoroacetate salt of D-tryptophan benzyl ester instead of L-alanine methyl ester hydrochloride. Column chromatography (silica 20% ethyl acetate and 80% dichloromethane) led to the separate diastereomers the high rF material diastereomer 1 and the low rF material diastereomer 2.

b. endo-cis-7-(2-R-(3-indolyl)-1-carboxy-ethylaminocarbonyl)-8-(1-adamantylmethylaminocarbonyl)-5,6-benzobicyclo[2.2.2]oct -2-ene (Diastereomer 1)

The reaction was performed essentially as described in example 9 step b. but using diastereomer 1 described in step a. above as substrate instead of the compound of example 9 step a. The compound was characterised and tested as the N-methyl-D-glucamine salt. Found: C, 59.92; H, 7.55; N, 6.19. $C_{43}H_{56}N_4O_9$. $5.5 H_2O$ requires C, 59.23; H, 7.74; N, 6.43%.

EXAMPLE 16

Preparation of endo-cis-7-(2-R-(3-indolyl)-1-carboxy-ethylaminocarbonyl)-8-(1-adamantylmethylaminocarbonyl)-5,6-benzobicyclo[2.2.2]oct-2-ene (Diastereomer 2)

The reaction was performed essentially as described in example 9 step b. but using diastereomer 2 described in example 15 step a. as substrate instead of the compound of example 9 step a. The compound was characterised and tested as the N-methyl-D-glucamine salt. Found: C, 63.61; H, 7.62; N, 6.72. $C_{43}H_{56}N_4O_9$. $2.25 H_2O$ requires C, 63.50: H, 7.50; N, 6.89%.

EXAMPLE 17

Preparation of exo-cis-7-(2-R-(3-indolyl)-1-carboxy-ethylaminocarbonyl)-8-(1-adamantylmethylaminocarbonyl)-5,6-benzobicyclo[2.2.2]oct-2-ene (Diastereomer 1)

The compound was prepared as in example 15 but using the compound of example 1 as substrate in step a. rather than the compound of example 2. The compound was characterised and tested as the N-methyl-D-glucamine salt. Found: C, 63.58; H, 7.55; N, 6.76. $C_{43}H_{56}N_2O_9$. $2.25 H_2O$ requires C, 63.50; H, 7.50; N, 6.89%.

EXAMPLE 18

Preparation of exo-cis-7-(2-R-(3-indolyl)-1-carboxy-ethylaminocarbonyl)-8-(1-adamantylmethylaminocarbonyl)-5,6-benzobicyclo[2.2.2]oct -2-ene (Diastereomer 2)

The reaction was performed essentially as described in example 16 but using diastereomer 2 described in example 17 step a. as substrate instead of diastereomer 2 of example 15 step a. The compound was characterised and tested as the N-methyl-D-glucamine salt. Found: C, 63.58; H, 7.55; N, 6.76. $C_{43}H_{56}N_4O_9$. 2.25 $H_2O$ requires C, 63.50; H, 7.50; N, 6.89%.

EXAMPLE 19

Preparation of exo-cis-7-(1-S-Methoxycarbonyl-ethylaminocarbonyl)-8-(1-adamantylmethylaminocarbonyl)-2,3-dimethyl-5,6-benzobicyclo[2.2.2]oct-2-ene (mixture of diastereomers)

The compound was prepared essentially as in example 7 but using the product of example 11 as substrate instead of the product of example 1 found: C, 73.65; H, 8.06; N, 5.57. $C_{31}H_{40}N_2O_4$ requires C, 73.78; H, 7.99; N, 5.55%.

EXAMPLE 20

Preparation of endo and exo cis-7-(2-R-carboxypyrrolidinocarbonyl)-8-(1-adamantylmethylaminocarbonyl)-2,3-benzo-5,6-(2,3-naphtho)bicyclo[2.2.2]octane (mixture of diastereomers)

The compound was prepared essentially as in example 9 but using the product of example 14 as substrate instead of the product of example 1 in step a. The compound was characterised and tested as the N-methyl-D-glucamine salt.

Found: C, 65.38; H, 7.47; N, 5.13. $C_{45}H_{57}N_3O_9$. 2.34 $H_2O$ requires C, 65.43; H, 7.53; N, 5.09%.

EXAMPLE 21

Preparation of endo and exo cis-7-(2-S-methoxy-carbonylpyrrolidinocarbonyl)-8-(1-adamantylmethylaminocarbonyl)-2,3-benzo-5,6-(2,3-naphtho) bicyclo-[2.2.2]octane (mixture of diastereomers)

The compound was prepared essentially as in example 20 but using L-proline methyl ester as substrate instead of D-Proline benzyl ester in the coupling step. Obviously no hydrogenation was necessary. Found: C, 73.53; H, 6.93; N, 4.81. $C_{39}H_{42}N_2O_4$. 1.72 $H_2O$ requires C, 73.91; H, 7.23; N, 4.42%.

EXAMPLE 22

Preparation of endo-cis-7-(1-S-Methoxycarbonyl-ethylaminocarbonyl)-8-(1-adamantylmethylaminocarbonyl)-2,3-benzobicyclo[2.2.2]octane (mixture of diastereomers)

The compound of example 8 (60 mg, 0.126 mmol) was dissolved in dry THF (10 ml) and Adams catalyst (20 mg) was added. The mixture was stirred under an atmosphere of hydrogen for 18 h and then filtered through a plug of celite and evaporated to leave a colourless solid (38 mg, 63%) found: C, 72.16; H, 8.05; N, 5.79. $C_{29}H_{38}N_2O_4$. 0.23 $H_2O$ requires C, 72.15; H, 8.03; N, 5.80%.

EXAMPLE 23

Preparation of exo-cis-7-(1-S-Methoxycarbonyl-ethylaminocarbonyl)-8-(1-adamantylmethylaminocarbonyl)-2,3-benzobicyclo[2.2.2]octane (mixture of diastereomers)

The reaction was performed essentially as in example 22 but using the product of example 7 as substrate rather than the product of example 8 found: C, 72.76; H, 8.2; N, 5.79. $C_{29}H_{38}N_2O_4$ requires C, 72.77; H, 8.00: N, 5.85%.

EXAMPLE 24

Preparation of endo-cis-2-(1-S-Methoxycarbonyl-ethylaminocarbonyl)-3-(1-adamantylmethylaminocarbonyl)-bicyclo[2.2.2]oct-5-ene (mixture of diastereomers)

a. endo-cis-(±)-3-(1-adamantylmethylaminocarbonyl)-bicyclo[2.2.2]oct-5-ene-3-carboxylic acid endo-Bicyclo[2.2.2]oct-5-ene-2,3-dicarboxylic anhydride (1.0 g, 5.6 mmol) was dissolved in THF (30 ml) and 1-adamantylmethylamine (0.93 g, 5.6 mmol) was added. The mixture was heated at reflux briefly and then cooled to room temperature whereupon it was stirred for a further hour. The reaction mixture was filtered, washed with THF and ether and then dried to give the target compound (1.86 g, 97%)

b. endo-cis-2-(1-S-Methoxycarbonyl-ethylaminocarbonyl)-3-(1-adamantylmethylaminocarbonyl)-bicyclo[2.2.2]oct-5-ene (mixture of diastereomers)

The reaction was performed as in example 7 but using the product from step a. above as substrate instead of the product of example 1.

EXAMPLE 25

Preparation of cis-(±)-2-(1-S-Methoxycarbonyl-ethylaminocarbonyl)-3-(1-adamantylmethylaminocarbonyl)-bicyclo[2.2.2]octane The reaction was performed essentially as in example 22 but using the product of example 24 as substrate rather than the product of example 8. Found: C, 58.90; H, 7.88; N, 5.2. $C_{25}H_{38}N_2O_4$. 1.2 mol DCM requires C, 59.10; H, 7.88; N, 5.2%.

EXAMPLE 26

Preparation of endo-cis-7-(2-S-carboxy-pyrrolidinocarbonyl)-8-(1-adamantylmethylaminocarbonyl)-5,6-benzo-bicyclo[2.2.2]oct-2-ene (mixture of diastereomers)

The compound was prepared essentially as in example 10 but using L-proline benzyl ester as substrate rather than D-proline benzyl ester in step a. The compound was characterised and tested as the N-methyl-D-glucamine salt.

Found: C, 60.00; H, 8.04; N, 5.03. $C_{37}H_{53}N_3O_9$. 1.0 mol dioxan. 2.7 mol $H_2O$ requires C, 60.01; H, 8.16; N, 5.12%.

EXAMPLE 27

Preparation of exo-cis-7-(2-S-carboxy-pyrrolidinocarbonyl)-8-(1-adamantylmethylaminocarbonyl)-5,6-benzo-bicyclo[2.2.2]oct-2-ene (mixture of diastereomers)

The compound was prepared essentially as in example 9 but using L-proline benzyl ester as substrate rather than D-proline benzyl ester in step a. The compound was characterised and tested as the N-methyl-D-glucamine salt.

Found: C, 60.41; H, 7.99; N, 5.34. $C_{37}H_{53}N_2O_9$. 3.0 mol $H_2O$ requires C, 60.17; H, 8.06; N, 5.69%.

EXAMPLE 28

Preparation of endo-cis -7-(2-R-carboxy-4-R-hydroxy-pyrrolidinocarbonyl)-8-(1-adamantylmethylaminocarbonyl)-5,6-benzo-bicyclo[2.2.2]oct -2-ene (mixture of diastereomers)

The compound was prepared essentially as in example 10 but using cis-D-hydroxy-proline benzyl ester as substrate rather than D-proline benzyl ester in step a. The compound was characterised and tested as the N-methyl-D-glucamine salt.

Found: C, 60.54; H, 7.65; N, 4.82. $C_{37}H_{53}N_3O_{10}$. 1.3 mol dioxan. 1.1 mol $H_2O$ requires C, 60.76; H, 7.93; N, 5.04%.

EXAMPLE 29

Preparation of exo-cis-7-(2-R-carboxy-4-R-hydroxy-pyrrolidinocarbonyl)-8-(1-adamantylmethylaminocarbonyl)-5,6-benzo-bicyclo[2.2.2]oct -2-ene (mixture of diastereomers)

The compound was prepared essentially as in example 9 but using cis-D-hydroxyproline benzyl ester as substrate rather than D-proline benzyl ester in step a. The compound was characterised and tested as the N-methyl-D-glucamine salt.

Found: C, 58.32; H, 7.67; N, 5.18. $C_{37}H_{53}N_3O_{10}$. 3.6 mol $H_2O$ requires C, 58.11; H, 7.94; N, 5.49%.

EXAMPLE 30

Preparation of endo-cis-7-(2-S-methoxycarbonyl-pyrrolidinocarbonyl)-8-(1-adamantylmethylaminocarbonyl)-5,6-benzo-bicyclo[2.2.2]oct-2-ene (mixture of diastereomers)

The compound of example 26 (100 mg, 0.205 mmol) was dissolved in methanol (20 ml) and trested with an ethereal solution of diazomethane. Acetic acid was added to decompose extra diazomethane and the solution evaporated to leave the title compound as a colourless solid. Found: C, 71.61; H, 8.34; N, 5.13. $C_{31}H_{38}N_2O_4$. 1.3 mol MeOH requires C, 71.27; H, 8.00; N, 5.15%.

EXAMPLE 31

Preparation of exo-cis-7-(2-S-methoxycarbonyl-pyrrolidinocarbonyl)-8-(1-adamantylmethylaminocarbonyl)-5,6-benzo-bicyclo[2.2.2]oct-2-ene (mixture of diastereomers)

The compound was prepared essentially as in example 30 but using the compound of example 27 as substrate rather than the compound of example 26. Found: C, 72.30; H, 8.15; N, 5.03. $C_{31}H_{38}N_2O_4$. 0.9 mol MeOH requires C, 72.09; H, 7.89; N, 5.27%.

EXAMPLE 32

Preparation of exo-cis-7-(2-R-methoxycarbonyl-pyrrolidinocarbonyl)-8-(1-adamantylmethylaminocarbonyl)-5,6-benzo-bicyclo[2.2.2]oct-2-ene (mixture of diastereomers)

The compound was prepared essentially as in example 30 but using the compound of example 9 as substrate rather than the compound of example 26. Found: C, 66.04; H, 7.15; N, 4.81. $C_{31}H_{38}N_2O_4$. 0.6 mol MeOH. 0.8 mol DCM requires C, 65.98; H, 7.18; N, 4.75%.

EXAMPLE 33

Preparation of cis-(±)-2-(1-R-carboxy-pyrrolidinocarbonyl)-3-(1-adamantylmethylaminocarbonyl)-bicyclo[2.2.2]oct-5-ene The reaction was performed as in example 9 but using the product from example 24 step a. in step a. as substrate instead of the product of example 1. The compound was characterised and tested as the N-methyl-D-glucamine salt.

Found: C, 54.29; H, 8.68; N, 4.86. $C_{33}H_{53}N_3O_9$. 1.3 mol Dioxan. 5.2 mol $H_2O$ requires C, 54.36; H, 8.81; N, 4.98%.

EXAMPLE 34

Preparation of endo-cis-7-(2-R-carboxy-pyrrolidinocarbonyl)-8-(1-adamantylmethylaminocarbonyl)-2-oxo-5,6-benzobicyclo[2.2.2]octane (mixture of diastereomers 1)

The compound was prepared essentially as in example 9 but using the product of example 13 step a. as substrate instead of the product of example 1 in step a. The product of step a. was separated into two fractions by column chromatography (silica, 25% ethyl acetate and 75% dichloromethane). The less polar material was converted into the title compound.

The compound was further characterised and tested as the N-methyl-D-glucamine salt. Found: C, 59.96; H, 7.80; N, 5.59. $C_{37}H_{53}N_3O_{10}$.2.3 $H_2O$ requires C, 59.95; H, 7.83; N, 5.67%.

EXAMPLE 35

Preparation of endo-cis-7-(2-R-carboxy-pyrrolidinocarbonyl)-8-(1-adamantylmethylaminocarbonyl)-2-oxo-5,6-benzobicyclo[2.2.2]octane (mixture of diastereomers 2)

The compound was prepared essentially as in example 34 but using the more polar material isolated from the column chromatography in the final step.

The compound was further characterised and tested as the N-methyl-D-glucamine salt. Found: C, 49.05; H, 6.69; N, 4.29. $C_{37}H_{53}N_2O_{10}$. 3.1 $H_2O$.2.6 $SiO_2$ requires C, 48.73; H, 6.54; N, 4.61%.

EXAMPLE 36

Preparation of (±)-endo-cis-8-(1-adamantylmethylaminocarbonyl)-2-(±)-benzyl-5,6-benzobicyclo[2.2.2]octane-7-carboxylic acid (mixture of regioisomers).

a. (±)- endo-dimethyl-2-oxo-5,6-benzobicyclo[2.2.2]octane-7,8-dicarboxylate

The compound of example 9 step a. (10.7 g, 4.4 mmole) was dissolved in methanol (200 ml) and concentrated sulphuric acid (0.5 ml) was added. The solution was heated at reflux for 5 h and then cooled and evaporated to a low volume (approx. 20 ml). The oil was taken up in diethyl ether and washed with 10% sodium carbonate solution (2×20 ml) and then dried, filtered and evaporated. The residual oil was taken up in acetone (100 ml) and 4-toluenesulphonic acid (0.8 g) was added. The solution was heated at reflux for 1 h, and then evaporated. The oil was triturated with diethyl ether to leave the title compound as a white solid (5.8 g).

b. (±)-endo-dimethyl-2-hydroxy-2-benzyl-5,6-benzobicyclo-[2.2.2]octane-7,8-dicarboxylate Powdered samarium (6.0 g, 40 mmol) was placed in a flask under dry nitrogen. A solution of 1,2-diiodoethane (5.64 g, 20 mmol) in dry THF (400 ml) was added dropwise over 1 h. The reaction mixture was stirred for a further hour in which time a deep blue solution was formed. The product of step a. (5.76 g, 40 mmol) was added in dry THF (20 ml) followed by benzyl bromide (3.82 g, 22mmol). The mixture was stirred at room temperature for 2 h. The blue solution was decanted from the samarium metal and diluted with 1M hydrochloric acid (400 ml). This solution was extracted with diethyl ether (2×200 ml). The combined organic layer was washed with water, 10% sodium thiosulphate solution and brine and dried. After fitraton and evaporation a white foam was left (7.56 g) which was the title compound.

c. (±)-endo-dimethyl-2-benzyl-5,6-benzobicyclo[2.2.2]oct-2-ene-7,8-dicarboxylate The product of step b. (700 mg, 1.9 mmol) was dissolved in benzene(10 ml)and 4-toluenesulphonic acid (80 mg, 0.42 mmol) was added. The solution was stirred and refluxed for 2.5 h in the presence of 4A molecular sieves. The mixture was diluted with ethyl acetate (20 ml) and washed with 10% sodium hydrogencarbonate solution (20 ml) and brine (20 ml). The solution was dried, filtered and evaporated to leave a material that was purified by column chromatography (silica ethyl acetate and hexane 2:1). This left the title compound (250 mg) as a cis/trans mixture of double bonds.

d. (±)-endo-dimethyl -2-benzyl -5,6-benzobicyclo[2.2.2] octane-7,8-dicarboxylate The product of step c. (200 mg, 0.6 mmol) was dissolved in methanol (10 ml) and 5% platinum on carbon catalyst (30 mg) was added. Hydrogen was introduced to the flask. The catalyst was removed by fitration through celite and the filtrate was evaporated to leave the title compound as a colourless oil (200 mg).

e. (±)-endo-2-benzyl-5,6-benzobicyclo[2.2.2]octane-7,8-dicarboxylic acid

The product of step d. (200 mg, 0.6 mmol) was dissolved in ethanol (5 ml) and sodium hydroxide (100 mg, 2.5 mmol) in water (1 ml) was added. The mixture was heated at reflux for 2 h. The solution was cooled and evaporated to low volume and acidified with 2M hydrochloric acid solution. The aqueous layer was then extracted with ethyl acetate (10 ml) and the organic layer was washed with brine. The ethyl acetate layer was dried, filtered and evaporated to leave the title compound (144 mg).

f. (±)-endo-2-benzyl-5,6-benzobicyclo[2.2.2]octane-7,8-dicarboxylic acid anhydride.

The product of step e. (2.15 g, 6.4 mmol) and acetic anhydride (5 ml) were heated at 120° for 1 h. The excess acetic anhydride was removed by distillation at 70° and 0.1 mm Hg to leave the title compound 2.0 g g. (±)-endo-cis-8-(1-adamantylmethylaminocarbonyl)-2-(±)-benzyl-5,6-benzobicyclo[2.2.2]octane-7-carboxylic acid.

The product of step f. (2.0 g, 6 mmol) was dissolved in dry THF (20 ml) and triethylamine (1.0 ml) was added. This was followed by 1-adamantylmethylamine (1.16 g, 0.6 mmol) and the reaction mixture stirred at room temperature for 1 h. The reaction mixture was diluted with ethyl acetate (30 ml) and extracted with 1M hydrochloric acid. The organic phase was extracted with brine, dried, filtered and evaporated and purified by column chromatography (silica 95% ethyl acetate and 5% acetone). This left the title compound (256 mg) as a white solid.

The compound was further characterised and tested as the N-methyl-D-glucamine salt. Found: C, 69.2; H, 8.02; N, 4.13. $C_{39}H_{54}N_2O_8$. requires C, 69.00; H, 8.11; N, 4.10%.

EXAMPLE 37

Preparation of cis-7-(2R-carboxymethylaminocarbonyl-pyrrolidinocarbonyl)-8-(1-adamantylmethylaminocarbonyl)-2,3-benzo-5,6-(2,3-naphtho)bicyclo[2.2.2]octane (mixture of diastereomers 1)

a. cis-7-(2R-benzyloxycarbonylmethylaminocarbonyl-pyrrolidinocarbonyl)-8-(1-adamantylmethylaminocarbonyl)-2,3-benzo-5,6-(2,3-naphtho ) bicyclo[2.2.2]octane The product of example 14 (164 mg, 0.33 mmol) was dissolved in dichloromethane (40 ml) and D-prolyl-glycine benzyl ester trifluoroacetate salt (121 mg, 0.33 mmol), Hunigs base (0.18 ml, 1 mmol) and PyBOP (174 mg, 0.33 mmol) were added. The solution was stirred for 84 h at room temperature and then washed sequentially with 2M hydrochloric acid (20 ml), saturated sodium hydrogencarbonate solution (20 ml) and saturated brine (20 ml). The solution was dried, filtered and evaporated and then purified by column chromatography (silica and ethyl acetate) to give two fractions. The less polar material ($R_{1\ 0.7}$) was the compound of this example (71 mg)(product a). The more polar material ($R_f$ 0.3) was designated product b (68 mg).

b. cis -7-(2R-carboxymethylaminocarbonyl -pyrrolidinocarbonyl)-8-(1-adamantylmethylaminocarbonyl)-2,3-benzo-5,6-(2,3-naphtho)bicyclo[2.2.2]octane (mixture of diastereomers 1)

This was prepared as in example 9 step b. but using the compound of step a. above instead of the product of example 9 step a.

The compound was further characterised and tested as the N-methyl-D-glucamine salt. Found: C, 48.80; H, 6.18; N, 4.81. $C_{47}H_{60}N_4O_{10}$.3.9 $H_2O$. 4.2 Silica requires C, 48.51; H, 5.87; N, 4.81%.

EXAMPLE 38

Preparation of cis-7-(2R-carboxymethylaminocarbonyl-pyrrolidinocarbonyl)-8-(1-adamantylmethylaminocarbonyl) -2,3-benzo-5,6-(2,3-naphtho)bicyclo[2.2.2]octane (mixture of diastereomers 2)

This was prepared as in example 9 step b. but using the compound of example 37 step a. product b instead of the product of example 9 step a.

The compound was further characterised and tested as the N-methyl-D-glucamine salt. Found: C, 52.42; H, 6.87; N, 5.07. $C_{47}H_{60}N_4O_{10}$.6.2 $H_2O$. 2.1 Silica requires C, 52.32; H, 6.76; N, 5.19%.

EXAMPLE 39

Preparation of (±)-endo and exo-cis-7-(1-adamantylmethylaminocarbonyl)-2-diphenylmethylene bicyclo-[2.2.1]hept-4-ene-6-carboxylic acid.

a. endo and exo cis-2-diphenylmethylene bicyclo[2.2.1] hept-4-ene-6,7-dicarboxylic acid anhydride.

Diphenylfulvene (1.15 g, 5 mol), maleic anhydride (0.6 g, 6 mol) and hydroquinone (10 mg) were dissolved in toluene (10 ml) and stirred at reflux overnight. After cooling the mixture was evaporated and the residue was taken up in a minimum volume of hot toluene, and an equal volume of hexane was added. After cooling pale yellow cystals were formed which were isolated by filtration. These were washed with hexane and dried in vacuo to yield the title compound (1.45 g).

b. (±)-endo and exo-cis-7-(1-adamantylmethylaminocarbonyl)-2-diphenylmethylene bicyclo[2.2.1]hept-4-ene-6-carboxylic acid The product was prepared essentially as in example 36 step g. except that the product of step a. above was used as substrate instead of the product of example 36 step f. The final compound was a 2:1 mixture of endo and exo products but absolute structure could not be assigned.

The compound was further characterised and tested as the N-methyl-D-glucamine salt. Found: C, 70.00; H, 7.90; N, 4.2. $C_{40}H_{52}N_2O_8$. requires C, 69.74; H, 7.61; N, 4.2%.

EXAMPLE 40

Preparation of cis-exo-7-(2R-(1S-carboxyethylaminocarbonyl)-pyrrolidinocarbonyl)-8-(1-adamantylmethylaminocarbonyl)-2,3-benzobicyclo-[2.2.2.] octane a. cis-exo-7-(2R-(1S-benzyloxycarbonylethyl-
aminocarbonyl)-pyrrolidinocarbonyl)-8-(1-
adamantylmethylaminocarbonyl)-2,3-benzobicyclo
[2.2.2]oct-2-ene This was prepared essentially as in example 7 but using D-prolyl-L-alanine benzyl ester as substrate instead of L-alanine methyl ester hydrochloride.

b. cis-exo-7-(2R-(1S-carboxyethylaminocarbonyl)-
pyrrolidino-carbonyl)-8-(1-
adamantylmethylaminocarbonyl)-2,3-benzo-bicyclo
[2.2.2]octane This was prepared essentially as in example 22 except that the substrate from step a. above was used instead of the compound of example 8.

The compound was further characterised and tested as the N-methyl-D-glucamine salt.

EXAMPLE 41

Preparation of cis-exo-7-(2R-(1R-carboxyethylaminocarbonyl)-pyrrolidinocarbonyl)-8-(1-adamantylmethylaminocarbonyl)-2,3-benzobicyclo[2.2.2] octane The compound was prepared essentially as in example 40 except that D-prolyl-D-alanine benzyl ester was used as substrate instead of D-prolyl-L-alanine benzyl ester in step a.

The compound was further characterised and tested as the N-methyl-D-glucamine salt.

EXAMPLE 42

Preparation of cis-exo-7-(2R-carboxymethylaminocarbonyl-pyrrolidinocarbonyl)-8-(1-adamantylmethylaminocarbonyl)-2,3-benzobicyclo[2.2.2] octane The compound was prepared essentially as in example 40 except that D-prolyl-glycine benzyl ester was used as substrate instead of D-prolyl-L-alanine benzyl ester in step a.

The compound was further characterised and tested as the N-methyl-D-glucamine salt.

EXAMPLE 43

Preparation of cis-exo-7-(2S-(1S-carboxyethylaminocarbonyl)-pyrrolidinocarbonyl)-8-(1-adamantylmethylaminocarbonyl)-2,3-benzobicyclo[2.2.2] octane The compound was prepared essentially as in example 40 except that L-prolyl-L-alanine benzyl ester was used as substrate instead of D-prolyl-L-alanine benzyl ester in step a.

The compound was further characterised and tested as the N-methyl-D-glucamine salt.

EXAMPLE 44

Preparation of cis-exo-7-(2S-(1R-carboxyethylaminocarbonyl)-pyrrolidinocarbonyl)-8-(1-adamantylmethylaminocarbonyl)-2,3-benzobicyclo[2.2.2] octane The compound was prepared essentially as in example 40 except that L-prolyl-D-alanine benzyl ester was used as substrate instead of D-prolyl-L-alanine benzyl ester in step a.

The compound was further characterised and tested as the N-methyl-D-glucamine salt.

EXAMPLE 45

Preparation of cis-exo-7-(2R-carboxymethylaminocarbonylpyrrolidinocarbonyl)-8-(1-adamantylmethylaminocarbonyl)-2,3-benzobicyclo[2.2.2] octane The compound was prepared essentially as in example 40 except that L-prolyl-glycine benzyl ester was used as substrate instead of D-prolyl-L-alanine benzyl ester in step a.

The compound was further characterised and tested as the N-methyl-D-glucamine salt.

EXAMPLE 46

Preparation os cis-endo-7-(2R-carboxymethylaminocarbonyl-pyrrolidinocarbonyl)-8-(1-adamantylmethylaminocarbonyl)-2,3-benzobicyclo[2.2.2] octane a. cis-endo-7-(2R-benzyloxycarbonylmethylaminocarbonyl-
pyrrolidinocarbonyl)-8-(1-
adamantylmethylaminocarbonyl)-2,3-benzobicyclo
[2.2.2]oct-2-ene This was prepared essentially as in example 8 but using D-prolyl-glycine benzyl ester as substrate instead of L-alanine methyl ester hydrochloride.

b. cis-endo-7-(2R-(1S-carboxyethylaminocarbonyl)-
pyrrolidinocarbonyl)-8-(1-
adamantylmethylaminocarbonyl)-2,3-benzobicyclo
[2.2.2]octane.

This was prepared essentially as in example 22 except that the substrate from step a. above was used instead of the compound of example 8.

The compound was further characterised and tested as the N-methyl-D-glucamine salt.

EXAMPLE 47

Preparation of cis-endo-7-(2R-(1R-carboxyethylaminocarbonyl)-pyrrolidinocarbonyl)-8-(1-adamantylmethylaminocarbonyl)-2,3-benzobicyclo[2.2.2] octane The compound was prepared essentially as in example 46 except that D-prolyl-D-alanine benzyl ester was used as substrate instead of D-prolyl-glycine benzyl ester in step a.

The compound was further characterised and tested as the N-methyl-D-glucamine salt.

EXAMPLE 48

Preparation of cis-endo-7-(2R-(1S-carboxyethylaminocarbonyl)-pyrrolidinocarbonyl)-8-(1-adamantylmethylaminocarbonyl)-2,3-benzobicyclo[2.2.2] octane The compound was prepared essentially as in example 46 except that D-prolyl-L-alanine benzyl ester was used as substrate instead of D-prolyl-glycine benzyl ester in step a.

The compound was further characterised and tested as the N-methyl-D-glucamine salt.

EXAMPLE 49

Preparation of cis-endo-7-(2S-carboxymethylaminocarbonyl-pyrrolidinocarbonyl)-8-(1-adamantylmethylaminocarbonyl)-2,3-benzobicyclo[2.2.2] octane The compound was prepared essentially as in example 46 except that L-prolylglycine benzyl ester was used as substrate instead of D-prolyl-glycine benzyl ester in step a.

The compound was further characterised and tested as the N-methyl-D-glucamine salt Found: C, 56.76; H, 8.15; N, 7.05. $C_{39}H_{58}N_4O_{10} \cdot 4.4\ H_2O$ requires C, 57.00; H, 8.19; N, 6.82%.

EXAMPLE 50

Preparation of cis-endo-7-(2S-(1R-carboxyethylaminocarbonyl)-pyrrolidinocarbonyl)-8-(1-adamantylmethylaminocarbonyl)-2,3-benzobicyclo[2.2.2] octane The compound was prepared essentially as in example 46 except that L-prolyl-D-alanine benzyl ester was used as substrate instead of D-prolyl-glycine benzyl ester in step a.

The compound was further characterised and tested as the N-methyl-D-glucamine salt. Found: C, 58.51; H, 8.25; N, 4.61. $C_{40}H_{60}N_4O_{10}$·4.9 $H_2$. 0.6 silica requires C, 58.45; H, 8.16; N, 4.57%.

EXAMPLE 51

Preparation of cis-endo-7-(2S-(1S-carboxyethylaminocarbonyl)-pyrrolidinocarbonyl)-8-(1-adamantylmethylaminocarbonyl)-2,3-benzobicyclo[2.2.2]octane The compound was prepared essentially as in example 46 except that L-prolyl-L-alanine benzyl ester was used as substrate instead of D-prolyl-glycine benzyl ester in step a.

The compound was further characterised and tested as the N-methyl-D-glucamine salt. Found: C, 52.22; H, 7.64; N, 5.96. $C_{40}H_{60}N_4O_{10}$·4.9 $H_2O$. 1.2 dichloromethane requires C, 52.25; H, 7.68; N, 5.92%.

EXAMPLE 52

Preparation of cis-endo-7-(2S-(1R-carboxyethylaminocarbonylmethyl)-pyrrolidinocarbonyl)-8-(1-adamantylmethylaminocarbonyl)-2,3-benzobicyclo[2.2.2]octane The compound was prepared essentially as in example 46 except that L-pyrrolidinomethylcarbonyl-D-alanine benzyl ester was used as substrate instead of D-prolyl-glycine benzyl ester in step a.

The compound was further characterised and tested as the N-methyl-D-glucamine salt.

EXAMPLE 53

Preparation of cis-(±)-exo-6-(2R-carboxy-pyrrolidinocarbonyl)-7-(1-adamantylmethylaminocarbonyl)-2,2-diphenylbicyclo[2.2.1]hept-4-ene a. exo-2,2-diphenylbicyclo[2.2.1]hept-4-ene-6,7-dicarboxylic acid anhydride.

1,1-diphenylcyclopentadiene (prepared as in J.A.C.S., 1990, 112, 6695)(900 mg, 3.9 mmol) and maleic anhydride (425 mg, 4.3 mmol) were dissolved in toluene (10 ml) and stirred and heated at 85°overnight. Hexane (20 ml) was added to the warm solution and upon cooling a pale yellow crystalline solid was formed. This was isolated by filtration, washed with a small quantity of hexane and dried to yield the title compound (470 mg).

b. (±)-exo-cis-7-(1-adamantylmethylaminocarbonyl)-2,2-diphenylbicyclo[2.2.1] hept-4-ene-6-carboxylic acid.

This compound was prepared essentially as in example 36 step g. except that the product of step a. of this example was used as substrate instead of the compound of example 36 step f.

c. cis-(±)-exo-6-(2R-carboxy-pyrrolidinocarbonyl)-7-(1-adamantylmethylaminocarbonyl)-2,2-diphenylbicyclo[2.2.1] hept -4-ene This compound was prepared essentially as in example 9 except that the product of step b. was used as substrate instead of the compound of example 1 and the t-butyl ester of D-proline was used instead of the benzyl ester. Deprotection was carried out by use of trifluoroacetic acid in dichloromethane.

The compound was further characterised and tested as the N-methyl-D-glucamine salt. Found: C, 65.11; H, 7.67; N, 5.40. $C_{44}H_{59}N_3O_9$·2$H_2O$ requires C, 65.25; H, 7.84; N, 5.19%.

EXAMPLE 54

Preparation of 1-methoxycarbonyl-endo-cis-(±)-7-(1-adamantylmethylaminocarbonyl)-2,3-benzobicyclo-[2.2.1]hept-6-carboxylic acid a. 1-methoxycarbonyl-endo-cis-(±)-2,3-benzobicyclo-[2.2.1]hept-6,7-dicarboxylic acid anhydride.

Methyl 1-indenecarboxylate (12.5 g, 71.5 mmol) and maleic anhydride (14.02 g, 143mmol) were heated together in xylene (90 ml) at reflux for 24 h. The solution was allowed to cool to room temperature and evaporated to a volume of about 20 ml. Diethyl ether (20 ml) was added and the solution was left to stand for 1 h. The crystalline precipitate was filtered, washed with diethyl ether and dried to leave the title compound (11.36 g, 58%).

b. 1-methoxycarbonyl-endo-cis-(±)-7-(1-adamantylmethylaminocarbonyl)-2,3-benzobicyclo[2.2.1]hept-6-carboxylic acid This compound was prepared essentially as in example 36 step g. except that the product of step a. of this example was used as substrate instead of the compound of example 36 step f.

The compound was further characterised and tested as the N-methyl-D-glucamine salt. Found: C, 61.84; H, 8.11; N, 4.07. $C_{33}H_{48}N_2O_{10}$ 0.64 $H_2O$ requires C, 61.52; H, 7.71; N, 4.35%.

EXAMPLE 55

Preparation of (±)-1-methoxycarbonyl-endo-cis-6-(1S-(3,5-dicarboxyphenylaminocarbonyl)-2-phenylethylaminocarbonyl)-7-(1-adamantylmethylaminocarbonyl)-2,3-benzo-bicyclo[2.2.1]heptane This compound was prepared essentially as in example 9 except that the product of example 54 was used as substrate instead of the compound of example 1 and 1S-(3,5-dibenzyloxycarbonylphenylaminocarbonyl)-2-phenylethylamine was used instead of the benzyl ester of D-proline in step a.

The compound was further characterised and tested as the di N-methyl-D-glucamine salt. Found: C, 57.55; H, 7.44; N, 4.45. $C_{57}H_{79}N_5O_{19}$ 1.6 $H_2O$. 4.1 dioxan requires C, 57.68; H, 7.58; N, 4.58%.

EXAMPLE 56

Preparation of (±)-1-methoxycarbonyl-endo-cis-6-(2R-carboxypyrrolidinocarbonyl)-7-(1-adamantylmethylaminocarbonyl)-2,3-benzobicyclo[2.2.1]heptane This compound was prepared essentially as in example 9 except that the product of example 54 was used as substrate instead of the compound of example 1.

The compound was further characterised and tested as the N-methyl-D-glucamine salt. Found: C, 53.14; H, 7.58; N, 3.55. $C_{38}H_{55}N_3O_{11}$ 2.2 dichloromethane and 4.1 dioxan requires C, 53.2; H, 7.29; N, 3.27%.

EXAMPLE 57

Preparation of endo-cis-(±)-7-(1-adamantylmethylaminocarbonyl)-2,3-benzobicyclo[2.2.1]hept-6-carboxylic acid a. endo-cis-(±)-2,3-benzobicyclo[2.2.1]hept-6,7-dicarboxylic acid anhydride.

Indene (40.4 g, 348 mmol), maleic anhydride (24.12 g, 246 mmol) and hydroquinone (1.5 g) were heated together in tetralin (35 ml) at reflux for 4.5 h under an atmosphere of argon. The solution was allowed to cool to 120° and poured cautiously into ethyl acetate (100 ml) and the resulting solution poured into toluene (300 ml) with stirring. The ethyl acetate was removed by evaporation and toluene (100 ml) was added. The solution was heated and the polymer was removed by filtraton. The solution was then cooled to -10° and the crystalline product was isolated by filtration. This left the title compound (8.24 g).

b. endo-cis-(±)-7-(1-adamantylmethylaminocarbonyl)-2,3-benzobicyclo[2.2.1]hept-6-carboxylic acid This compound was prepared essentially as in example 36 step g. except that the product of step a. of this example was used as substrate instead of the compound of example 36 step f.

The compound was further characterised and tested as the N-methyl-D-glucamine salt. Found: C, 62.00; H, 8.43; N, 4.10. $C_{31}H_{46}N_2O_8$ 2.0 dioxan requires C, 62.37; H, 8.32; N, 3.73%.

EXAMPLE 58

Preparation of (±)-endo-cis-6-(1S-(3,5-dicarboxyphenylaminocarbonyl)-2-phenyl-ethylaminocarbonyl)-7-(1-adamantylmethylaminocarbonyl)-2,3-benzobicyclo-[2.2.1] heptane This compound was prepared essentially as in example 55 except that the product of example 57 was used as substrate instead of the compound of example 54 in step a. The compound was further characterised and tested as the di N-methyl-D-glucamine salt.

EXAMPLE 59

Preparation of (±)-endo-cis-6-(2R-carboxy-pyrrolidinocarbonyl)-7-(1-adamantylmethylaminocarbonyl)-2,3-benzobicyclo[2.2.1]heptane This compound was prepared essentially as in example 9 except that the product of example 57 was used as substrate instead of the compound of example 1.

The compound was further characterised and tested as the N-methyl-D-glucamine salt. Found: C, 53.14; H, 7.58; N, 3.55. $C_{38}H_{55}N_3O_{11}$ 2.2 dichloromethane and 4.1 dioxan requires C, 53.2; H, 7.29; N, 3.27%.

EXAMPLE 60

Preparation of exo-cis-7-(1S-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene This compound was prepared essentially as in example 9 except that 1S-(3,5-dibenzyloxycarbonylphenylaminocarbonyl)-2-phenyl-ethylamine was used instead of the benzyl ester of D-proline in step a.

The compound was further characterised and tested as the di N-methyl-D-glucamine salt. Found: C, 57.04; H, 7.76; N, 5.97. $C_{56}H_{77}N_5O_{17}$ 5.0 $H_2O$ requires C, 56.85; H, 7.42; N, 5.92%.

EXAMPLE 61

Preparation of exo-cis-7-(1S-(3,5-dicarboxyphenylaminocarbonyl)-2-phenyl-ethylaminocarbonyl)-8-(1-adamantylmethylaminocarbonyl)-2,3-benzobicyclo[2.2.2]octane The compound was prepared essentially as in example 40 except that 1S-(3,5-dibenzyloxycarbonylphenylaminocarbonyl)-2-phenyl-ethylamine was used as substrate instead of D-prolyl-L-alanine benzyl ester in step a.

The compound was further characterised and tested as the di N-methyl-D-glucamine salt. Found: C, 58.90; H, 7.81; N, 6.22. $C_{56}H_{79}N_5O_{17}$ 2.8 $H_2O$ 0.4 dioxan requires C, 58.63; H, 7.50; N, 5.94%.

EXAMPLE 62

Preparation of endo-cis-7-(1S-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene This compound was prepared essentially as in example 10 except that 1S-(3,5-dibenzyloxycarbonylphenylaminocarbonyl)-2-phenyl-ethylamine was used instead of the benzyl ester of D-proline in step a.

The compound was further characterised and tested as the di N-methyl-D-glucamine salt.

EXAMPLE 63

Preparation of endo-cis-7-(1S-(3,5-dicarboxyphenylaminocarbonyl)- 2-phenyl-ethylaminocarbonyl)-8-(1-adamantylmethylaminocarbonyl)-2,3-benzobicyclo[2.2.2]octane The compound was prepared essentially as in example 46 except that 1S-(3,5-dibenzyloxycarbonylphenylaminocarbonyl)-2-phenyl-ethylamine was used as substrate instead of D-prolyl-glycine benzyl ester in step a.

The compound was further characterised and tested as the di N-methyl-D-glucamine salt. Found: C, 58.90; H, 7.81; N, 6.22. $C_{56}H_{79}N_5O_{17}$ 2.8 $H_2O$ 0.4 dioxan requires C, 58.63; H, 7.50; N, 5.94%.

EXAMPLE 64

Preparation of exo-cis-7-(1R-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene This compound was prepared essentially as in example 9 except that 1R-(3,5-dibenzyloxycarbonylphenylaminocarbonyl)-2-phenyl-ethylamine was used instead of the benzyl ester of D-proline in step a.

The compound was further characterised and tested as the di N-methyl-D-glucamine salt.

EXAMPLE 65

Preparation of endo-cis-7-(1R-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene This compound was prepared essentially as in example 10 except that 1R-(3,5-dibenzyloxycarbonylphenylaminocarbonyl)-2-phenyl-ethylamine was used instead of the benzyl ester of D-proline in step a.

The compound was further characterised and tested as the di N-methyl-D-glucamine salt.

EXAMPLE 66

Preparation of (±)-endo-cis-6-(1R-(3,5-dicarboxyphenylaminocarbonyl)-2-phenylethylaminocarbonyl)-7-(1-adamantylmethylaminocarbonyl)-2,3-benzobicyclo[2.2.1]heptane This compound was prepared essentially as in example 55 except that the product of example 57 was used as substrate instead of the compound of example 54 in step a, and the 1R isomer of 1-(3,5-dibenzyloxycarbonylphenylaminocarbonyl)-2-phenyl-ethylamine was used instead of the 1S.

The compound was further characterised and tested as the di N-methyl-D-glucamine salt.

EXAMPLE 67

Preparation of exo-cis-7-(1S-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene a. (±)-exo-cis-8-(1-naphthylmethylaminocarbonyl)-5,6-benzobicyclo[2.2.2]oct-2-ene-7-carboxylic acid The compound was prepared essentially as in example 1 step b. but using 1-naphthylmethylamine as substrate instead of 1-adamantylmethylamine.

b. exo-cis-7-(1S-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene The compound was prepared essentially as in example 60 except that the compound of example 67 step a. above was used as substrate in step a. instead of the compound of example 1.

The compound was further characterised and tested as the di N-methyl-D-glucamine salt.

EXAMPLE 68

Preparation of exo-cis-7-(1R-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene The compound was prepared essentially as in example 64 except that the compound of example 67 step a. was used as substrate in step a. instead of the compound of example 1.

The compound was further characterised and tested as the di N-methyl-D-glucamine salt.

EXAMPLE 69

Preparation of endo-cis-7-(1S-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene a. (±)-8-endo-cis-(1-naphthylmethylaminocarbonyl)-5,6-benzobicyclo[2.2.2]oct-2-ene-7-carboxylic acid The compound was prepared essentially as in example 2 step b. but using 1-naphthylmethylamine as substrate instead of 1-adamantylmethylamine.

b. endo-cis-7-(1S-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene The compound was prepared essentially as in example 60 except that the compound of example 69 step a. above was used as substrate in step a. instead of the compound of example 1.

The compound was further characterised and tested as the di N-methyl-D-glucamine salt.

EXAMPLE 70

Preparation of endo-cis-7-(1R-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene The compound was prepared essentially as in example 64 except that the compound of example 69 step a. was used as substrate in step a. instead of the compound of example 1.

The compound was further characterised and tested as the di N-methyl-D-glucamine salt.

EXAMPLE 71

Preparation of (±)-1-methoxycarbonyl-endo-cis-6-(1R-(3,5-dicarboxyphenylaminocarbonyl)-2-phenyl-ethylaminocarbonyl)-7-(1-adamantylmethylaminocarbonyl)-2,3-benzo-bicyclo[2.2.1]heptane The compound was prepared essentially as in example 9 except that the product of example 54 was used as substrate instead of the compound of example 1 and 1R-(3,5-dibenzyloxycarbonylphenylaminocarbonyl)-2-phenyl-ethylamine was used instead of the benzyl ester of D-proline in step a.

The compound was further characterised and tested as the di N-methyl-D-glucamine salt.

EXAMPLE 72

Preparation of cis-exo-7-(2S-(1R-carboxyethylaminocarbonylmethyl)-pyrrolidinocarbonyl)-8-(1-adamantylmethylaminocarbonyl)-2,3-benzobicyclo[2.2.2]octane The compound was prepared essentially as in example 40 except that L-pyrrolidinomethylcarbonyl-D-alanine benzyl ester was used as substrate instead of D-prolyl-glycine benzyl ester in step a.

The compound was further characterised and tested as the N-methyl-D-glucamine salt.

The following $^1$H NMR data were obtained for the compounds described in the examples:

Ex.1a (exo isomer)(d$^6$-DMSO) δ 7.4–7.1 (4H, m), 6.7 (2H, dd), 4.5 (2H, m), 3.4 (2H, m).

Ex.1a (endo isomer)(d$^6$-DMSO) δ 7.2–7.1 (4H, m), 6.7 (2H, dd), 4.4 (2H, m), 3.4 (2H, m).

Ex.1b (d$^6$-DMSO) δ 10.5 (1H, br s), 7.6 (1H, t), 7.2 (2H, m), 7.0 (2H, m), 6.5 (1H, t), 6.3 (1H, t), 4.1 (1H, d), 4.0 (1H, d), 2.9–2.5 (4H, m), 1.9 (3H, s), 1.6 (6H, q), 1.4 (6H, s).

Ex.2 (d$^6$-DMSO) δ 11.2 (1H, br s), 7.4 (1H, t), 7.2 (1H, m), 6.9 (3H, m), 6.5 (2H, m), 4.0 (1H, d), 3.9 (1H, d), 3.1 (1H, d), 2.6 (2H, m), 2.4 (1H, m), 1.9 (3H, s), 1.6 (6H, q), 1.4 (6H, s).

Ex.3 (d$^6$-DMSO) δ 11.4 (1H, br s), 7.8 (1H, t), 7.2 (2H, m), 7.0 (2H, m), 6.5 (1H, t), 6.3 (1H, t), 4.1 (1H, d), 3.9 (1H, d), 2.8–2.6 (4H, m), 1.7–0.7 (11H, m).

Ex.4 (d$^6$-DMSO) δ 11.4 (1H, br s), 7.7 (1H, t), 7.2–6.9 (4H, m), 6.6 (2H, m), 4.0 (1H, d), 3.9 (1H, d), 3.1–2.6 (4H, m), 1.7–0.8 (11H, m).

Ex.5 (d$^6$-DMSO) δ 11.8 (1H, br s), 7.8 (1H, t), 7.2 (2H, m), 7.0 (2H, m), 6.5 (1H, t), 6.3 (1H, t), 4.1 (1H, d), 3.9 (1H, d), 3.0–2.6 (4H, m), 1.4–0.8 (15H, m).

Ex.6 (d$^6$-DMSO) δ 11.4 (1H, br s), 7.6 (1H, t), 7.2–6.9 (4H, m), 6.6 (2H, m), 4.0 (1H, d), 3.9 (1H, d), 3.0–2.7 (4H, m), 1.4–0.8 (15H, m).

Ex.7 (CDCl$_3$) δ 7.2–7.1 (4H, m), 6.9–6.0 (4H, m), 4.4, (1H, m), 4.2 (2H, m), 3.7 (3H, 2×s), 3.2–2.5 (4H, m), 2.0 (3H, s), 1.6 (6H, q), 1.4 (6H, s), 1.3 (3H, 2×d).

Ex.8 (CDCl$_3$) δ 7.4–7.1 (4H, m), 6.6 (2H, m), 6.0, 5.7, 5.3 and 5.0 (2H, 4×m), 4.3, (1H, m), 4.2 (2H, m), 3.7 (3H, s), 3.2–3.0 (2H, m), 2.8–2.4 (2H, m), 2.0 (3H, s), 1.6 (6H, q), 1.4 (6H, s), 1.1 (3H, 2×d).

Ex.9 (d$^6$-DMSO), 7.6 (1H, t), 7.2 (6H, m), 4.3–4.1 (1H, m), 3.5–3.0 (6H, m), 2.8–2.2 (4H, m), 2.0 (3H, s), 1.6 (6H, q), 1.4 (6H, s), 1.0 (2H, m).

Ex.10 (d$^6$-DMSO), 12.5 (1H, br s), 7.2 (6H, m), 5.9 (1H, t), 4.5–4.1 (1H, m), 3.8–2.9 (6H, m), 2.7–2.2 (4H, m), 2.0 (3H, s), 1.6 (6H, q), 1.4 (8H, m).

Ex.11 b (d$^6$-DMSO) δ 11.5 (1H, br s), 7.6 (1H, t), 7.2 (2H, m), 7.0 (2H, m), 3.8 (1H, d), 3.6 (1H, d), 2.9 2H, m), 2.6 (2H, m), 1.9 (3H, s), 1.8 (3H, m), 1.6 (9H, m), 1.4 (6H, s).

Ex.12 (d$^6$-DMSO) δ 11.5 (1H, br s), 7.4 (1H, t), 7.2 (1H, m), 6.9 (3H, m), 3.7 (1H, d), 3.6 (1H, d), 3.1 (1H, dd), 2.7–2.4 (3H, m), 1.9 (3H, s), 1.8–1.5 (12H, m), 1.4 (6H, s).

Ex.13a (de-DMSO) δ 7.3 (4H, m), 3.94 (3H, m), 3.87 (1H, m), 2.6 (1H, m), 2.2(1H, d).

Ex.13b (d$^6$-DMSO) δ 11.3 (1H, br s), 7.7 (1H, m), 7.2 (4H, m), 3.6–3.2 (4H, m), 2.6 (2H, m), 2.1 (1H, m), 1.9 (3H, s), 1.6 (6H, q), 1.4 (6H, s).

Ex.14a (d$^6$-DMSO) δ 8.0–7.8 (10H,m), 5.0 (2H, s), 3.8 (2H, s).

Ex.14b (de-DMSO) δ 11.2 (1H,s), 7.9–6.9 (11H,m), 4.6 (1H,s), 4.5 (1H,s), 3.3–2.6 (4H,m), 1.9 (3H,s), 1.6 (6H,q), 1.4 (6H,s).

Ex.15b (CDCl$_3$) δ 8.6 (1H, s), 7.6–7.0 (9H, m), 6.6 (2H, m), 6.1 (1H, br s), 5.6 (1H, br s), 4.6 (1H, m), 4.0–2.9 (6H, m), 2.6 (1H, m), 2.4 (1H, m), 1.9 (3H, s), 1.6 (6H, q), 1.3 (6H, d).

Ex.16 (CDCl$_3$) δ 8.6 (1H, s), 7.6–6.8 (12H, m), 5.4 (1H, br s), 4.6 (1H, m), 4.0–2.9 (6H, m), 2.6 (1H, m), 2.4 (1H, m), 1.9 (3H, s), 1.6 (6H, q), 1.3 (6H, d).

Ex.17 (CDCl$_3$) δ 8.4 (1H, s), 7.6–7.0 (12H, m), 6.1 (1H, br s), 4.8 (1H, m), 4.0 (1H, m), 3.4–2.9 (5H, m), 2.6 (1H, m), 2.4 (1H, m), 1.9 (3H, s), 1.6 (6H, q), 1.3 (6H, d).

Ex.18 (CDCl$_3$) δ 8.6 (1H, s), 7.6–6.9 (11H, m), 6.6 (1H, m), 6.4 (1H, br s), 4.8 (1H, m), 3.4–2.9 (6H, m), 2.6 (1H, m), 2.4 (1H, m), 1.9 (3H, s), 1.6 (6H, q), 1.3 (6H, d).

Ex.19 (d$^6$-DMSO) δ 8.6 (1H, s), 7.6–6.9(11H, m), 6.6 (1H, m), 6.4 (1H, br s), 4.8 (1H, m), 3.4–2.9 (6H, m), 2.6 (1H, m), 2.4 (1H, m), 1.9 (3H, s), 1.6 (6H, q), 1.3 (6H, d).

Ex.20 (d$^6$-DMSO) δ 13.0–12.0 (1H, br-s), 7.9–6.9 (11H, m), 4.6 (2H, m), 4.2 (1H, m) 3.5–3.1 (4H, m), 2.9–2.6 (2H, m), 1.9 (7H, m), 1.6 (6H, q), 1.3 (6H, s).

Ex.21 (d$^6$-DMSO) δ 7.9–6.8 (11H, m), 4.6 (2H, m), 4.2–4.0 (1H, m), 3.6 (3H, 2×s), 3.5–3.1 (4H, m), 2.9–2.6 (2H, m), 1.9 (7H, m), 1.6 (6H, q), 1.3 (6H, s).

Ex.22 (d$^6$-DMSO) δ 8.0–6.1 (6H, m), 4.0 (1H, m), 3.6 (3H, s), 3.4–2.9 (8H,m), 2.6 (1H, m), 2.4 (1H, m), 1.9 (3H, m), 1.6 (6H, q), 1.3 (9H, m).

Ex.23 (d$^6$-DMSO) δ 7.9 (1H, d), 7.3 (1H, t), 7.1 (4H, s), 4.2 (1H, m), 3.6 (3H, s), 3.2–2.2 (10H, m), 1.9 (3H, m), 1.6 (6H, q), 1.3 (6H, s), 0.9 (3H, m).

Ex.24b (d$^6$-DMSO) δ 7.0–6.1 (4H, s), 4.1 (1H, m), 3.6 (3H, 2×s), 3.2–2.2 (10H, m), 1.9 (3H, m), 1.6 (6H, q), 1.3 (6H, s), 1.0 (3H, m).

Ex.25 (d$^6$-DMSO) δ 7.7 (1H, 2×d), 7.1 (1H, 2×t), 4.2 (1H, m), 3.6 (3H, s), 2.8–2.5 (2H, m), 2.7 (2H, m), 1.9–1.3 (25H, m), 1.2 (3H, m).

Ex.26 (d$^6$-DMSO) δ 12.5 (1H, br-s), 7.2 (6H, m), 5.9 (1H, t), 4.5–4.1 (1H, m), 3.8–2.9 (6H, m), 2.7–2.2 (2H, m), 1.9 (7H, m), 1.6 (6H, q), 1.3 (6H, s).

Ex.27 (d$^6$-DMSO) δ 12.5 (1H, br-s), 7.6 (1H, t), 7.2 (6H, m), 4.3–4.1 (1H, m), 3.5–2.9 (6H, m), 2.8–2.2 (4H, m), 1.9 (7H, m), 1.6 (6H, q), 1.4 (6H, s).

Ex.28 (d$^6$-DMSO) δ 12.5 (1H, br-s), 7.6–6.9 (7H, m), 4.8–4.0 (3H, m), 3.5–2.8 (6H, m), 2.7–2.2 (2H, m), 1.9 (5H, m), 1.6 (6H, q), 1.3 (6H, m).

Ex.29 (d$^6$-DMSO) δ 12.5 (1H, br-s), 7.6 (1H, br s), 7.2 (6H, m), 5.0 (1H, m), 4.3–4.1 (2H, m), 3.5–2.9 (6H, m), 2.8–2.2 (4H, m), 1.9 (3H, m), 1.6 (6H, q), 1.4 (6H, s).

Ex.30 (d$^6$-DMSO) δ 7.2 (6H, m), 6.1 and 5.9 (1H, 2×t), 4.5–4.1 (1H, m), 3.9–2.9 (9H, m), 2.7–2.2 (2H, m), 1.9 (7H, m), 1.6 (6H, q), 1.2 (6H, s).

Ex.31 (d$^6$-DMSO) δ 7.6 (1H, t), 7.2 (6H, m), 4.5–4.1 (1H, m), 3.6–2.9 (9H, m), 2.8–2.2 (2H, m), 1.9 (7H, m), 1.6 (6H, q), 1.2 (6H, s).

Ex.32 (de-DMSO) δ 7.6–7.2 (7H, m), 4.6–4.1 (1H, m), 3.6–2.9 (9H, m), 2.8–2.2 (2H, m), 1.9 (7H, m), 1.6 (6H, q), 1.2 (6H, s).

Ex.34 (d$^6$-DMSO) δ 12.5 (1H, br s), 7.2 (5H, m), 4.5–4.1 (1H, m), 3.8–2.9 (10H, m), 2.1–1.8 (7H, m), 1.6 (6H, q), 1.4 (6H, m).

Ex.35 (d$^6$-DMSO) δ 12.5 (1H, br s), 7.2 (5H, m), 4.2–3.9 (1H, m), 3.7–3.2 (10H, m), 2.1–1.7 (7H, m), 1.6 (6H, q), 1.2 (6H, m).

Ex.36 (CDCl$_3$) δ 7.2 (9H, m), 6.1 (1H, s), 3.3 (2H, m), 3.1 (1H, m), 2.9 (2H, m), 2.6–2.3 (2H, m), 2.1–1.9 (5H, s), 1.6 (7H, q), 1.4 (6H, m), 0.8 (1H, d).

Ex.37 (d$^6$-DMSO) δ 12.5 (1H, s), 8.1 (1H, t), 7.8–6.9 (10H, m), 6.9 (1H, t), 4.6 (2H, m), 4.0 (1H, m), 3.7 (2H, m),3.4–3.1 (4H, m), 2.6 (4H, m), 1.9 (7H, m), 1.6 (6H, q), 1.3 (6H, m).

Ex.38 (d$^6$-DMSO) δ 12.6 (1H, s), 8.3 (1H, t), 7.8–6.9 (11H, m), 4.6 (2H, m), 4.2 (1H, m), 3.8–3.1 (4H, m), 2.6 (4H, m), 1.9 (7H, m), 1.6 (6H, q), 1.4 (6H, m).

Ex.39 (d$^6$-DMSO) δ 7.7–7.0 (11H, m), 6.5–6.1 (2H, m), 3.5–2.6 (6H, m), 1.9 (3H, s), 1.6 (6H, q), 1.4 (6H, m).

Ex.40 (d$^6$-DMSO) δ 12.5 (1H, br s), 8.2–7.1 (6H, m), 4.1 (2H, m), 3.5–2.9 (6H, m), 2.8–2.2 (2H, m), 1.9 (11H, m), 1.6 (6H, q), 1.4 (6H, m), 1.1 (3H, m).

Ex.41 (d$^6$-DMSO) δ 12.5 (1H, br s), 7.9 (1H, t) 7.2 (5H, m), 4.2 (1H, m), 4.1 (1H, m), 3.6–2.9 (6H, m), 2.8–2.2 (2H, m), 1.9 (7H, m), 1.6 (10H, q), 1.4 (6H, m), 1.2 (3H, m).

Ex.42 (d$^6$-DMSO) δ 12.5 (1H, br s), 8.0 (1H, t), 7.9 (1H, 7.2 (4H, m), 4.2 (1H, m), 3.6–2.9 (8H, m), 2.8–2.2 (2H, m), 2.0–1.7 (11H, m)., 1.6 (6H, q), 1.4 (6H, m).

Ex.43 (d$^6$-DMSO) δ 12.5 (1H, br s), 7.9 (1H, t) 7.2 (5H, m), 4.2 (1H, m), 4.1 (1H, m), 3.6–2.9 (6H, m), 2.8–2.2 (2H, m), 1.9 (7H, m), 1.6 (10H, q), 1.4 (6H, m), 1.2 (3H, m).

Ex.44 (d$^6$-DMSO) δ 12.5 (1H, br s), 8.2–7.1 (6H, m), 4.1 (2H, m), 3.5–2.9 (6H, m), 2.8–2.2 (2H, m), 1.9 (11H, m), 1.6 (6H, q), 1.4 (6H, m), 1.1 (3H, m).

Ex.45 (d$^6$-DMSO) δ 12.5 (1H, br s), 8.0 (1H, m), 7.9 (1H, t), 7.2 (4H, m), 4.2 (1H, m), 3.6–2.9 (8H, m), 2.8–2.2 (2H, m), 2.0–1.7 (11H, m), 1.6 (6H, q), 1.4 (6H, m).

Ex.46 (d$^6$-DMSO) δ 7.9–7.0 (5H, m), 5.9 (1H, t), 3.9 (1H, m), 3.6–3.1 (8H, m), 2.6–2.2 (2H, m), 1.9 (11H, m), 1.6 (6H, q), 1.2 (6H, s).

Ex.47 (d$^6$-DMSO) δ 7.8–7.0 (5H, m), 5.8 (1H, t), 4.1 (2H, m), 3.6–3.1 (6H, m), 2.6–2.2 (2H, m), 1.9 (11H, m), 1.6 (6H, q), 1.2 (9H, m).

Ex.48 (d$^6$-DMSO) δ 7.6–7.0 (5H, m), 5.8 (1H, t), 4.0 (2H, m), 3.6–3.1 (6H, m), 2.6–2.2 (2H, m), 1.9 (11H, m), 1.6 (6H, q), 1.2 (9H, m).

Ex.49 (d$^6$-DMSO) δ 8.0–7.0 (5H, m), 5.7 (1H, t), 4.1 (1H, m), 3.8–3.1 (8H, m), 2.6–2.2 (2H, m), 1.9 (11H, m), 1.6 (6H, q), 1.2 (6H, m).

Ex.50 (d⁶-DMSO) δ 7.5–6.9 (6H, m), 4.1 (2H, m), 3.6–3.1 (6H, m), 2.6–2.2 (2H, m), 1.9 (11H, m), 1.6 (6H, q), 1.2 (9H, m).

Ex.51 (d⁶-DMSO) δ 7.9–6.9 (5H, m), 5.8 (1H, m), 4.1 (2H, m), 3.6–3.1 (6H, m), 2.6–2.2 (2H, m), 1.9 (11H, m), 1.6 (6H, q), 1.2 (9H, m).

Ex.52 (d⁶-DMSO) δ 7.7–6.9 (5H, m), 6.3 and 5.8 (1H, 2×t), 4.0 (2H, m), 3.6–3.1 (5H, m), 2.6–2.2 (2H, m), 1.9 (11H, m), 1.6 (6H, q), 1.2 (9H, m Ex.53 (d⁶-DMSO) δ 7.6–6.8 (11H, m), 6.1 (1H, s), 5.8 m), 4.0 (3H, m), 3.3–2.5 (6H, m), 119 (7H, m), 1.6 (6H, q), 1.2 (6H, s).

Ex.54 (d⁶-DMSO) δ 11.4 (1H, br s), 7.5 (1H, t), 7.4–6.9 (4H, m), 3.7 (3H, s), 3.6 (3H, m), 2.5 (2H, 2×dd), 1.9 (5H, m), 1.6 (6H, q), 1.3 (6H, s).

Ex.55 (CDCl₃) δ 13.1 (2H, br s), 9.8 (1H, s), 8.3 (1H, s), 8.2 (1H, s), 8.1 (2H, m), 7.6–6.8 (10H, m), 4.5 and 4.3 (1H, 2×m) 3.8–2.7 (10H, m), 1.9 (5H, m), 1.6 (6H, q), 1.3 (6H, m).

Ex.56 (d⁶-DMSO) δ 12.0 (1H, br s), 8.0 (1H, m), 7.5–6.8 (4H, m), 4.1–3.0 (9H, m), 2.5 (2H, m), 1.9 (9H, m), 1.6 (6H, q), 1.3 (6H, m).

Ex.57 (d⁶-DMSO) δ 11.3 (1H, br s), 7.5 (1H, t), 7.2–6.8 (4H, m), 3.4 (6H, m), 2.5 (2H, 2xq), 1.9 (5H, m), 1.6 (6H, q), 1.3 (6H, s).

Ex.58 (CDCl₃) δ 13.1 (2H, br s), 9.8 (1H, s), 8.3 (1H, s), 8.2 (1H, s), 8.1 (2H, m), 7.6–6.8 (10H, m), 4.5 and 4.3 (1H, 2xm) 3.8–2.7 (10H, m), 1.9 (3H, m), 1.6 (6H, q), 1.3 (6H, m).

Ex.59 (d⁶-DMSO) δ 12.5 (1H, br s), 7.8 (1H, m), 7.3–6.7 (4H, m), 4.1–3.0 (9H, m), 2.5 (2H, m), 1.9 (7H, m), 1.6 (6H, q), 1.2 (6H, s).

Ex.60 (d⁶-DMSO) δ 13.0 (2H, br s), 10.1 and 9.9 (1H, 2×s), 8.6–7.0 (16H, m), 4.6 and 4.5 (1H, 2xm) 3.4–2.0 (8H, m), 1.9 (3H, m), 1.6 (6H, q), 1.3 (6H, m).

Ex.61 (d⁶-DMSO) δ 13.0 (2H, br s), 10.1 and 9.9 (1H, 2×s), 8.6–7.0 (14H, m), 4.6 and 4.5 (1H, 2xm) 3.4–1.9 (12H, m), 1.9 (3H, m), 1.6 (6H, q), 1.3 (6H, m).

Ex.62 (d⁶-DMSO) δ 13.0 (2H, br s), 9.9 (1H, s), 8.4 (1H, d), 8.2 (2H, s), 8.1 (1H, s) 7.4–6.6 (12H, m), 4.5 (1H, m) 3.3–2.9 (6H, m), 2.5–2.3 (2H, m), 1.9 (3H, m), 1.6 (6H, q), 0.9 (6H, m).

Ex.63 (d⁶-DMSO) δ 13.0 (2H, br s), 10.1 and 9.9 (1H, 2×s), 8.6–7.0 (14H, m), 4.6 and 4.5 (1H, 2xm) 3.4–1.9 (12H, m), 1.9 (3H, m), 1.6 (6H, q), 1.3 (6H, m).

Ex.64 (d⁶-DMSO) δ 13.0 (2H, br s), 10.1 and 9.9 (1H, 2×s), 8.6–7.0 (16H, m), 4.6 and 4.5 (1H, 2xm) 3.4–2.0 (8H, m), 1.9 (3H, m), 1.6 (6H, q), 1.3 (6H, m).

Ex.65 (d⁶-DMSO) δ 13.0 (2H, br s), 9.9 (1H, s), 8.4 (1H, d), 8.2 (2H, s), 8.1 (1H, s) 7.4–6.6 (12H, m), 4.5 (1H, m) 3.3–2.9 (6H, m), 2.5–2.3 (2H, m), 1.9 (3H, m), 1.6 (6H, q), 0.9 (6H, m).

Ex.66 (CDCl₃) δ 13.1 (2H, br s), 9.8 (1H, s), 8.3 (1H, s), 8.2 (1H, s), 8.1 (2H, m), 7.6–6.8 (10H, m), 4.5 and 4.3 (1H, 2xm) 3.8–2.7 (10H, m), 1.9 (3H, m), 1.6 (6H, q), 1.3 (6H, m).

Ex.67 (d⁶-DMSO) δ 13.0 (2H, br s), 10.1 and 9.9 (1H, 2×s), 8.6–7.0 (23H, m), 4.6 and 4.5 (1H, 2×m) 3.4–2.8 (6H, m), 2.5 (2H, m).

Ex.68 (d⁶-DMSO) δ 13.0 (2H, br s), 10.1 and 9.9 (1H, 2×s), 8.6–7.0 (23H, m), 4.6 and 4.5 (1H, 2×m) 3.4–2.8 (6H, m), 2.5 (2H, m).

Ex.69 (d⁶-DMSO) δ 13.0 (2H, br s), 10.1 and 9.9 (1H, 2×s), 8.6–7.0 (23H, m), 4.6 and 4.5 (1H, 2×m) 3.4–2.8 (6H, m), 2.5 (2H, m).

Ex.70 (d⁶-DMSO) δ 13.0 (2H, br s), 10.1 and 9.9 (1H, 2×s), 8.6–7.0 (23H, m), 4.6 and 4.5 (1H, 2×m) 3.4–2.8 (6H, m), 2.5 (2H, m).

Ex.71 (CDCl₃) δ 13.1 (2H, br s), 9.8 (1H, s), 8.3 (1H, s), 8.2 (1H, s), 8.1 (2H, m), 7.6–6.8 (10H, m), 4.5 and 4.3 (1H, 2xm), 3.8–2.7 (10H, m), 1.9 (5H, m), 1.6 (6H, q), 1.3 (6H, m).

Ex.72 (d⁶-DMSO) δ 7.7–6.9 (5H, m), 6.3 and 5.8 (1H, 2×t), 4.0 (2H, m), 3.6–3.1 (8H, m), 2.6–2.2 (2H, m), 1.9 (11H, m), 1.6 (6H, q), 1.2 (9H, m).

The compounds of the examples were tested for binding at the $CCK_B$ receptor in mouse cortical membranes by means of a radioligand binding assay. The procedure was as follows:

The whole brains from male mice (CD1 22–25 g; Charles River) were removed and placed in ice-cold buffer ($pH_{7.2}$ @ $21\pm3°$) of the following composition (mM); 10 HEPES, 130 NaCl, 4.7 KCl, 5 $MgCl_2$, 1 EDTA and containing 0.25 g.l⁻¹ bacitracin. The cortex was dissected, weighed and homogenised in 40 ml ice-cold buffer using a Teflon-in-glass homogeniser. The homogenate was centrifuged at 39,800 g for 20 min at @ 4°, the supernatant discarded and the pellet resuspended by homogenisation in fresh buffer. The homogenate was recentrifuged (39,800 g; 20 min @4°) and the final pellet was resuspended in HEPES buffer to give a tissue concentration of 2 mg.ml⁻¹ (original wet weight).

The membranes (400 ml) were incubated for 150 min at $21\pm3°$ in a final volume of 0.5 ml with HEPES buffer containing [$^{125}$I]-CCK8S (0.05 ml; 200 pM NEN 2200 Ci.mmol⁻¹) and competing compound. Total and non-specific binding of [$^{125}$I]-CCK8S were defined using 0.05 ml of buffer and 0.05 ml of 10 mM L-365,260, respectively. The assay was terminated by rapid filtration through pre-soaked Whatman GF/B filters using a Brandell Cell harvester. The filters were washed (3×3 ml) with ice-cold 50 mM Tris-$HC_1$ (pH7.4 @ 4° C.) and bound radioactivity determined by counting (1 min.) in a gamma-counter.

The results obtained from the CCKB assays are set out in Table 1.

TABLE 1

| Example | $CCK_B$ $pK_i$ | Example | $CCK_B$ $pK_i$ |
|---|---|---|---|
| 1 | 5.4 | 32 | 6.5 |
| 2 | 5.6 | 33 | 4.8 |
| 3 | 4.6 | 34 | 5.2 |
| 4 | 4.4 | 35 | 5.0 |
| 5 | 4.9 | 36 | 5.8 |
| 6 | 4.6 | 37 | 6.8 |
| 7 | 6.6 | 38 | 6.6 |
| 8 | 6.2 | 39 | 5.7 |
| 9 | 5.6 | 40 | 5.1 |
| 10 | 5.7 | 41 | 5.3 |
| 11 | 5.8 | 42 | 5.4 |
| 12 | 6.1 | 43 | 5.7 |
| 13 | 5.6 | 44 | 6.0 |
| 14 | 6.5 | 45 | 5.6 |
| 15 | 5.8 | 46 | 6.4 |
| 16 | 6.5 | 47 | 5.9 |
| 17 | 6.8 | 48 | 6.1 |
| 18 | 6.1 | 49 | 5.4 |
| 19 | 6.4 | 50 | 5.6 |
| 20 | 6.8 | 51 | 5.3 |
| 21 | 6.4 | 52 | 7.0 |
| 22 | 6.2 | 53 | 5.8 |
| 23 | 6.4 | 54 | 5.3 |
| 24 | 5.0 | 55 | 7.6 |
| 25 | 5.1 | 56 | 5.1 |
| 26 | 5.5 | 57 | 5.3 |

TABLE 1-continued

| Example | CCK$_B$ pK$_i$ | Example | CCK$_B$ pK$_i$ |
| --- | --- | --- | --- |
| 27 | 6.2 | 59 | 5.5 |
| 28 | 5.7 | 60 | 6.5 |
| 29 | 5.6 | 61 | 6.0 |
| 30 | 6.3 | | |

The compounds of the examples were also tested for gastrin antagonist activity in an immature rat stomach assay. The procedure was as follows:

The oesophagus of immature rats (33–50 g, ca. 21 days old) was ligated at the level of the cardiac sphincter and the duodenal sphincter was cannulated. The stomach was excised and flushed with ca. 1 ml of unbuffered physiological saline solution. The fundus was punctured and cannulated. A further 4–5 ml of unbuffered solution was flushed through the stomach to ensure the preparation was not leaking. The stomach was lowered into a jacketed organ bath containing 40 ml of buffered solution containing $3 \times 10^{-8}$ M 5-methyl-furmethide, maintained at 37° and gassed vigorously with 95% $O_2$/5% $CO_2$. The stomach was continuously perfused at a rate of 1 ml min$^{-1}$ with unbuffered solution gassed with 100% $O_2$ with the perfusate passing over an internally referenced pH-electrode fixed 12 cm above the stomach.

After 120 min of stabilisation the drugs were added directly to the serosal solution in the organ bath and after a further 60 min cumulative pentagastrin dose-response curves were started. Changes in acid secretion were monitored and the curves analysed according to Black et. al., Br. J. Pharmacol., 1985, 86, 581.

The results obtained from the gastrin assays are set out in Table 2.

TABLE 2

| Example | Gastrin pK$_B$ | Example | Gastrin pK$_B$ |
| --- | --- | --- | --- |
| 2 | 5.9 | 24 | 5.9 |
| 7 | 6.5 | 25 | 6.0 |
| 8 | 6.3 | 26 | 5.9 |
| 9 | 6.1 | 27 | 6.5 |
| 10 | 5.8 | 29 | 5.7 |
| 11 | 5.2 | 30 | 6.4 |
| 12 | 5.3 | 31 | 6.3 |
| 13 | 5.5 | 37 | 6.3 |
| 15 | 5.5 | 38 | 6.2 |
| 16 | 6.3 | 39 | 5.6 |
| 17 | 6.2 | 54 | 6.1 |
| 18 | 6.0 | 55 | 6.9 |
| 19 | 5.8 | 56 | 5.6 |
| 22 | 6.7 | 60 | 7.3 |
| 23 | 6.5 | 61 | 6.6 |

The compounds of the examples were also tested in a CCK$_A$ binding assay as follows:

The pancreatata were removed from male guinea-pigs (200–300 g; Dunkin Hartley) and placed in ice-cold HEPES buffer (pH 7.2 @ 21±3°). The pancreatata were homogenised in 40 ml ice-cold HEPES buffer using a polytron (Brinkmann, PT10, setting 10) 4×1 second. The homogenate was centrifuged at 39,800 g for 15 min at 4°. The supernatant was discarded and the pellet re-suspended using a Teflon-in-glass homogeniser in 20 volumes of fresh buffer and re-centrifuged as above. The final pellet was re-suspended using a Teflon-in-glass homogeniser to a tissue concentration of 1 mg.ml$^{-1}$ (original wet weight), and filtered through 500 µm pore-size Nytex mesh.

The membranes (400 µl ; containing 0.375 µM PD134, 308) are incubated for 150 minutes at 21±3° in a final volume of 0.5 ml with HEPES buffer containing [$^{125}$I]-CCK$_8$(S)(50 µl ; pM) and competing compound. Total and non-specific binding of [$^{125}$I]-CCK$_8$(S) are defined using 50 µl of buffer and 50 µl of 100 nM L-364,718 respectively. The assay is terminated by rapid filtration through pre-soaked Whatman GF/B filters using a Brandell Cell Harvester. The filters were washed (3×3 ml) with ice-cold 50 mM Tris HCl (pH 7.4 at 4°) and bound radioactivity is determined by counting (1 min) in a gamma counter.

The results are set out in Table 3.

TABLE 3

| Example | CCK$_A$ pK$_i$ | Example | CCK$_A$ pK$_i$ |
| --- | --- | --- | --- |
| 17 | 6.3 | 37 | 5.5 |
| 18 | 6.0 | 38 | 5.1 |
| 34 | 5.1 | 41 | 5.1 |
| 35 | 4.8 | 42 | 5.2 |
| 36 | 5.4 | 43 | 5.0 |

We claim:

1. A method of treating a patient in whom lowered gastrin or cholecystokinin activity therapeutically desirable comprising administering to said patient an amount effective for counteracting an effect of cholecystokinin or gastrin of a gastrin or cholecystokinin antagonist having the formula (I) below, or a pharmaceutically acceptable salt thereof

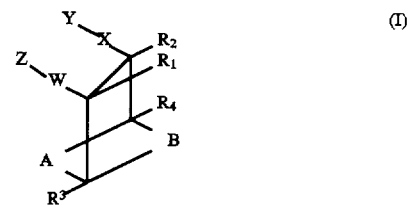

(I)

wherein A is selected from

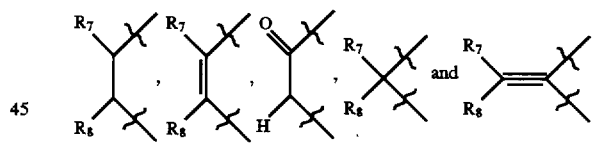

and B is

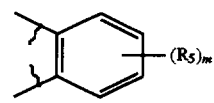

wherein:

W and X are carbonyl group, and X

Y is R$_9$—O— or R$_9$—N(R$_{10}$)—, wherein R$_9$ is H or C$_1$ to C$_{15}$ hydrocarbyl, up to two carbon atoms of the hydrocarbyl moiety optionally being replaced by a nitrogen, oxygen or sulphur atom provided that Y does not contain a —O— group, and R$_{10}$ is H, C$_1$ to C$_3$ alkyl, carboxymethyl or esterified carboxymethyl, Z is selected from i) —O—R$_{11}$ wherein R$_{11}$ is H, C$_1$ to C$_5$ alky, phenyl, substituted phenyl, benzyl or substituted benzyl;

ii)

wherein Q is H, $C_1$ to $C_5$ hydrocarbyl, or —$R_{12}$—U, wherein $R_{12}$ is a bond or $C_1$ to $C_3$ alkylene and U is aryl, substituted aryl, heterocyclic, or substituted heterocyclic;

iii)

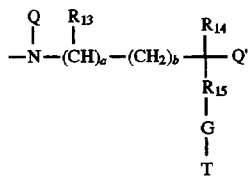

wherein a is 0 or 1 and b is from 0 to 3, $R_{13}$ is H or methyl, $R_{14}$ is H or methyl; or $R_{14}$ is $CH_2$= and Q' is absent; or $R_{13}$ and $R_{14}$ are linked to form a 3- to 7-membered ring, $R_{15}$ is a bond or $C_1$ to $C_5$ hydrocarbylene, G is a bond, —CHOH— or —C(O)—, Q' is as recited above for Q or —$R_{12}$—(C(O))$_d$—L—(C(O))$_e$—$R_{11}$ wherein $R_{11}$ and $R_{12}$ are as defined above, L is O, S or —N($R_{16}$)—, in which $R_{16}$ is as defined above for $R_{10}$, and d and e are 0 or 1, provided that d+e<2; or Q' and $R_{14}$, together with the carbon atom to which they are attached, form a 3- to 7-membered ring, Q' is as defined above; or Q and $R_{14}$ together form a group of the formula —(CH$_2$)$_f$—V—(CH$_2$)$_g$— wherein V is —S—, —S (O)$_2$—, —CH$_2$—, —CHOH— or —C(O)—, f is from 0 to 2 and g is from 0 to 3; or, when Q' is —$R_{12}$—U and U is an aromatic group, Q may additionally represent a methylene link to U, which link is ortho to the $R_{12}$ link to U, T is H, cyano, $C_1$ to $C_4$ alkyl, —CH$_2$OH, carboxy, esterified carboxy, amidated carboxy or tetrazolyl; or Z is absent and W is H, $R_1$ is H, methyl, halo, carboxy, esterified carboxy, amidated carboxy, tetrazolyl, carboxymethyl, esterified carboxymethyl, amidated carboxymethyl or tetrazolylmethyl, $R_2$ is selected from the groups recited above for $R_1$; or, when Z is absent and W is H, $R_2$ may additionally represent —C(O)—Z' wherein Z' is selected from the groups recited above for Z; or $R_1$ and $R_2$ together form a second bond between the carbon atoms to which they are attached, $R_3$ and $R_4$ are independently selected from hydrogen, halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_5$ is selected from halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_7$ and $R_8$ are independently selected from hydrogen, $C_1$ to $C_6$ alkyl, phenyl, benzyl, substituted phenyl and substituted benzyl, m is from 0 to 4, provided that m is not more than 2 unless $R_5$ is exclusively halo.

2. A pharmaceutical composition, comprising a therapeutically effective amount of a compound according to formula (II) below, or a pharmaceutically acceptable salt thereof, in combination with a pharmaceutically acceptable diluent or carrier,

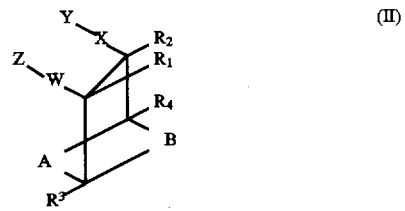

(II)

wherein A is selected from

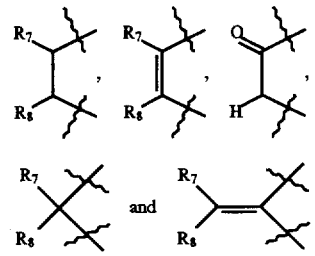

wherein:

W and X are carbonyl,

Y is $R_9$—O— or $R_9$—N($R_{10}$)— wherein $R_9$ is G $C_1$ to $C_{15}$ hydrocarbyl, up to two carbon atoms of the hydrocarbyl moiety optionally being replaced by a nitrogen, oxygen or sulphur atom provided that Y does not contain a —O—O— group, and $R_{10}$ is H, $C_1$ to $C_3$ alkyl, carboxymethyl or esterified carboxymethyl, Z is selected from i) —O—$R_{11}$ wherein $R_{11}$ is H, $C_1$ to $C_5$ alky, phenyl, substituted phenyl, benzyl or substituted benzyl;

ii)

wherein Q is H, $C_1$ to $C_5$ hydrocarbyl, or —$R_{12}$—U, wherein $R_{12}$ is a bond or $C_1$ to $C_3$ alkylene and U is aryl, substituted aryl, heterocyclic, or substituted heterocyclic, iii)

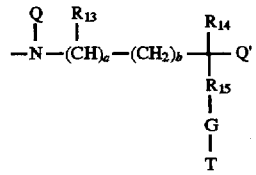

wherein a is 0 or 1 and b is from 0 to 3, $R_{13}$ is H or methyl, $R_{14}$ is H or methyl; or $R_{14}$ is $CH_2$= and Q' is absent; or $R_{13}$ and $R_{14}$ are linked to form a 3- to 7-membered ring, $R_{15}$ is a bond or $C_1$ to $C_5$ hydrocarbylene, G is a bond, —CHOH—or —C(O)—, Q' is as recited above for Q or —$R_{12}$—(C(O))$_d$—L—(C(O))$_e$—$R_{11}$ wherein $R_{11}$ and $R_{12}$ are as defined above, L is O, S or —N($R_{16}$)—, in which $R_{16}$ is as defined above for $R_{10}$, and d and e are 0 or 1, provided that d+e<2; or Q' and $R_{14}$, together with the carbon atom to which they are attached, form a 3- to 7-membered ring, Q is as defined above; or Q and $R_{14}$ together form a group of the formula —(CH$_2$)$_f$—V—(CH$_2$)$_g$— wherein V is —S—, —S(O)$_2$—, —CH$_2$—, —CHOH— or —C(O)—, f is from 0 to 2 and g is from 0 to 3; or, when Q' is —$R_{12}$—U and U is an aromatic group, Q may additionally represent a methylene link to U, which link is ortho to the $R_{12}$ link to U, T is H, cyano, $C_1$ to $C_4$ alkyl, —CH$_2$OH, carboxy, esterified carboxy, amidated carboxy or tetrazolyl; or $R_1$ is H, methyl, halo, carboxy, esterified carboxy, amidated carboxy, tetrazolyl, carboxymethyl, esterified carboxymethyl, amidated carboxymethyl or tetrazolylmethyl, $R_2$ is selected from the groups recited above for $R_1$; or, $R_1$ and $R_3$ together form a second bond between the carbon atoms to which they are attached, $R_3$ and $R_4$ are independently selected from hydrogen, halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_5$ is selected from halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_7$ and $R_8$ are independently selected from hydrogen, $C_1$ to $C_6$ alkyl, phenyl, benzyl, substituted phenyl and substituted benzyl, m is from 0 to 4, provided that m is not more than 2 unless $R_5$ is exclusively halo.

n is from 0 to 4, provided that n is not more than 2 unless $R_6$ is exclusively halo.

3. An isolated and purified compound according to formula (III) below, or a pharmaceutically acceptable salt thereof,

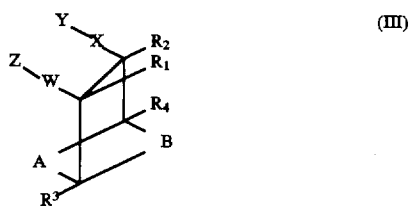

(III)

wherein A is selected from

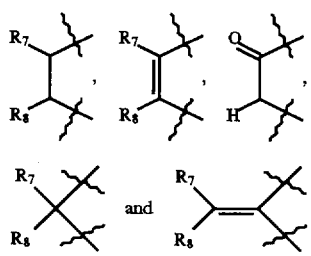

and B is

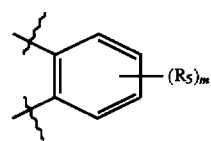

wherein
W and X are carbonyl J and K,

Y is $R_9$—O— or $R_9$—N($R_{10}$)—, wherein $R_9$ is H or $C_1$ to $C_{15}$ hydrocarbyl, up to two carbon atoms of the hydrocarbyl moiety optionally being replaced by a nitrogen, oxygen or sulphur atom provided that Y does not contain a —O—O— group, and $R_{10}$ is H, $C_1$ to $C_3$ alkyl, carboxymethyl or esterified carboxymethyl, Z is selected from
i) —O—$R_{11}$
wherein $R_{11}$ is H, $C_1$ to $C_5$ alkyl, phenyl, substituted phenyl, benzyl or substituted benzyl;
ii)

wherein Q is H, $C_1$ to $C_5$ hydrocarbyl, or —$R_2$—U, wherein $R_{12}$ is a bond or $C_1$ to $C_3$ alkylene and U is aryl, substituted aryl, heterocyclic, or substituted heterocyclic,
iii)

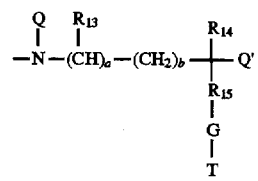

wherein
a is 0 or 1 and b is from 0 to 3,
$R_{13}$ is H or methyl,
$R_{14}$ is H or methyl; or $R_{14}$ is CH$_2$=and Q' is absent; or $R_3$ and $R_N$ are linked to form a 3-to 7-membered ring,
$R_{15}$ is a bond or $C_1$ to $C_5$ hydrocarbylene,
G is a bond, —CHOH—or —C(O)—
Q' is as recited above for Q or —$R_{12}$—(C(O))$_d$—L—(C(O))$_e$—$R_{11}$, wherein $R_{11}$ and $R_{12}$ are as defined above, L is O, S or —N($R_{16}$)—, in which $R_6$ is as defined above for Rio, and d and e are 0 or 1, provided that d+e<2; or Q' and $R_{14}$, together with the carbon atom to which they are attached, form a 3-to 7-membered ring, Q is as defined above; or Q and $R_N$ together form a group of the formula —(CH$_2$)$_f$—V—(CH$_2$)$_g$— wherein V is —S—, —S(O)$_2$—, —CH$_2$—, —CHOH— or —C(O)—, f is from 0 to 2 and g is from 0 to 3; or, when Q' is —$R_{12}$—U and U is an aromatic group, Q may additionally represent a methylene link to U, which link is ortho to the $R_2$ link to U, T is H, cyano, $C_1$ to $C_4$ alkyl, —CH$_2$OH, carboxy, esterified carboxy, amidated carboxy or tetrazolyl; or $R_1$ is H, methyl, halo, carboxy, esterified carboxy, amidated carboxy, tetrazolyl, carboxymethyl, esterified carboxymethyl, amidated carboxymethyl or tetrazolylmethyl, $R_2$ is selected from the groups recited above for $R_1$; or Rx and $R_2$ together form a second bond between the carbon atoms to which they are attached, $R_3$ and $R_4$ are independently selected from hydrogen, halo, amino, nitro, cyano, sulphamoyl, $C_1$ to $C_3$ alkyl, $C_1$ to $C_3$ alkoxy, carboxy, esterified carboxy, amidated carboxy or tetrazolyl, $R_5$ or each $R_5$ group, when m is 2 or more are independently selected from halo, amino, nitro, cyano, sulphamoyl, $C_1$ to $C_3$ alkyl, $C_1$ to $C_5$ alkoxy, carboxy, esterified carboxy, amidated carboxy or tetrazolyl, $R_7$ and $R_8$ are independently selected from hydrogen, $C_1$ to $C_6$ alkyl, phenyl, benzyl, substituted phenyl and substituted benzyl, m is from 0 to 4, provided that m not more than 2 unless $R_5$ is exclusively halo, and provided that —W—Z— is not equal to —X—Y—.

4. A compound according to claim 3 wherein $R_9$ is $C_6$ to $C_8$ straight or branched chain alkyl, or $R_{29}$—$(CH_2)_p$—, wherein $R_{29}$ is selected from phenyl, 1-naphthyl, 2-naphthyl, indolyl, norbonyl, adamantyl or cyclohexyl and p is from 0 to 3.

5. A compound according to claim 3 wherein $R_7$ and $R_8$ are both H.

6. A compound according to claim 3 wherein m is 0.

7. A compound selected from cis-endo-7-(2S-(1R-carboxyethylaminocarbonylmethyl)-pyrrolidinocarbonyl)-8-(1-adamantylmethylaminocarbonyl)-2,3-benzo-bicyclo[2.2.2]octane, (±)-1-methoxycarbonyl-endo-cis-6-(1S-3,5-dicarboxyphenylamiuocarbonyl)-2-phenylethylaminocarbonyl-7-(1-adamantylmethylaminocarbonyl)-2,3-benzobicyclo[2.2.1]heptane, (±)-endo-cis-6-(1S-(3,5-dicarboxyphenylaminocarbonyl)-2-phenyl-ethylaminocarbonyl)-7-(1-adamantylmethylaminocarbonyl)-2,3-benzobicyclo[2.2.1]heptane, exo-cis-7-(1S-(3,5S-dicarboxyphenylaminocarbonyl)-2-phenyl-ethylaminocarbonyl)-S-(1-adamantylmethylaminocarbonyl)-5,6-benzobicyclo[2.2.2]oct-2-ene, exo-cis-7-(1S-(3,5dicarboxyphenylaminocarbonyl)-2-phenyl-ethylaminocarbonyl-1)-S-(1-adamantylmethylaminocarbonyl)-2,3-benzobicyclo[2.2.2]octane, endo-cis-7-(1S-(3,5-dicarboxyphenylaminocarbonyl)-2-phenyl-ethylaminocarbonyl)-8-(1-adamantylmethylaminocarbonyl-5,6-benzobicyclo[2.2.2]oct-2-ene, endo-cis-7-(1S-(3,5-dicarboxyphenylaminocarbonyl)-2-phenyl-ethylaminocarbonyl)-S-(1-adamantylmethylaminocarbonyl)-2,3-benzobicyclo[2.2.2]octane, exo-cis-7-(1R-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene, endo-cis-7-(1R-(3,5-dicarboxyphenylaminocarbonyl)-2-phenyl-ethylaminocarbonyl)-8-(1-adamantylmethylaminocarbonyl)-5,6-benzobicyclo[2.2.2]oct-2-ene, (±)-endo-cis-6-(1R-(3,5-dicarboxyphenylaminocarbonyl)-2-phenyl-ethylaminocarbonyl)-7-(1-adamantylmethylaminocarbonyl)-2,3-benzobicyclo[2.2.1]heptane, exo-cis-7-(1S-(3,5-dicarboxyphenylaminocarbonyl)-3-phenyl-ethylaminocarbonyl)-S-(1-naphthylmethylaminocarbonyl)-5,6-benzobicyclo[2.2.2]oct-2-ene, exo-cis-7-(1R-(3,5-dicarboxyphenylaminocarbonyl)-2-phenyl-ethylaminocarbonyl)-8-(1-naphthylmethylaminocarbonyl)-5,6-benzobicyclo[2.2.2]oct-2-ene, endo-cis-7-(1S-(3,5-dicarboxyphenylaminocarbonyl)-2-phenyl-ethylaminocarbonyl)-S-(1-naphthylmethylaminocarbonyl)-5,6-benzobicyclo[2.2.2]oct-2-ene, endo-cis-7-(1R-(3,5-dicarboxyphenylaminocarbonyl)-2-phenyl -ethylaminocarbonyl)-8-(1-naphthylmethylaminocarbonyl)-5,6-benzobicyclo[2.2.2]oct -2-ene, (±)-1-methoxycarbonyl-endo-cis-6-(1R-(3,5-dicarboxyphenylaminocarbonyl)-1-phenyl-ethylamino-carbonyl)-7-(1-adamantylmethylaminocarbonyl)-2,3-benzobicyclo[2.2.1]heptane, and cis-exo-7-(2S-(1R-carboxyethylaminocarbonylmethyl)-pyrrolidinocarbonyl)-8-(1-adamantylmethylaminocarbonyl)-2,3-benzobicyclo[2.2.2]octane.

* * * * *